US010010276B2

(12) United States Patent
Al-Ali et al.

(10) Patent No.: US 10,010,276 B2
(45) Date of Patent: Jul. 3, 2018

(54) REGIONAL OXIMETRY USER INTERFACE

(71) Applicant: MASIMO CORPORATION, Irvine, CA (US)

(72) Inventors: Ammar Al-Ali, San Juan Capistrano, CA (US); Keith Ward Indorf, Riverside, CA (US); Faisal Kashif, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 683 days.

(21) Appl. No.: 14/507,660

(22) Filed: Oct. 6, 2014

(65) Prior Publication Data

US 2015/0099955 A1 Apr. 9, 2015

Related U.S. Application Data

(60) Provisional application No. 62/012,170, filed on Jun. 13, 2014, provisional application No. 61/887,878, (Continued)

(51) Int. Cl.
  *A61B 5/1455* (2006.01)
  *A61B 5/145* (2006.01)
  (Continued)

(52) U.S. Cl.
  CPC ........ *A61B 5/14542* (2013.01); *A61B 5/1455* (2013.01); *A61B 5/14552* (2013.01); *A61B 5/14553* (2013.01); *A61B 5/6833* (2013.01); *A61B 5/7275* (2013.01); *A61B 5/742* (2013.01); *A61B 5/746* (2013.01); *A61B 5/14551* (2013.01); *A61B 5/14557* (2013.01); *A61B 2562/22* (2013.01); *A61B 2562/222* (2013.01);
  (Continued)

(58) Field of Classification Search
  CPC .............. A61B 5/1455; A61B 5/14551; A61B 5/14553; A61B 5/74; A61B 5/742; A61B 5/746; A61B 5/7275
  See application file for complete search history.

(56) References Cited

U.S. PATENT DOCUMENTS 4,960,128 A 10/1990 Gordon et al.
4,964,408 A 10/1990 Hink et al.
(Continued)

OTHER PUBLICATIONS

US 8,845,543, 09/2014, Diab et al. (withdrawn)
US 9,579,050, 02/2017, Al-Ali (withdrawn)

*Primary Examiner* — Eric Winakur
(74) *Attorney, Agent, or Firm* — Knobbe Martens Olson & Bear LLP

(57) ABSTRACT

A regional oximetry system has a display and at least one processor causing a plurality of views to be displayed on the display, each configured to occupy at least a portion of the display. The views are adapted to present data responsive to at least one physiological signal. A first sensor port is configured to receive at least a first physiological signal representative of a regional tissue oxygenation level, and a second sensor port is configured to receive at least a second physiological signal representative of an arterial oxygen saturation level. One view presents a first trend graph of the first physiological signal and a second trend graph of the second physiological signal. An area between the first trend graph and the second trend graph can include a differential analysis of regional-to-central oxygen saturation.

12 Claims, 38 Drawing Sheets

Related U.S. Application Data filed on Oct. 7, 2013, provisional application No. 61/887,856, filed on Oct. 7, 2013, provisional application No. 61/887,883, filed on Oct. 7, 2013.

(51) Int. Cl.
 *A61B 5/00* (2006.01)
 *H01R 13/52* (2006.01)

(52) U.S. Cl.
 CPC ... *A61B 2562/225* (2013.01); *A61B 2562/227* (2013.01); *A61B 2562/228* (2013.01); *H01R 13/5224* (2013.01); *H01R 2201/12* (2013.01)

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| 393,830 A | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |

(56) References Cited

U.S. PATENT DOCUMENTS

| | | |
|---|---|---|
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |

(56) References Cited

U.S. PATENT DOCUMENTS

| | | |
|---|---|---|
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,584,345 B2 | 10/2013 | Al-Ali et al. |
| 8,577,431 B2 | 11/2013 | Lamego et al. |
| 8,581,732 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al- Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,761,851 B2 * | 6/2014 | Benni ................ A61B 5/14553 600/323 |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |

(56) References Cited

U.S. PATENT DOCUMENTS

| | | |
|---|---|---|
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |

(56) References Cited

U.S. PATENT DOCUMENTS

| | | |
|---|---|---|
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 2007/0282478 A1 | 12/2007 | Al-Ali et al. |
| 2009/0247924 A1 | 10/2009 | Lamego et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2009/0299157 A1 | 12/2009 | Telfort et al. |
| 2010/0004518 A1 | 1/2010 | Vo et al. |
| 2010/0030040 A1 | 2/2010 | Poeze et al. |
| 2010/0069725 A1 | 3/2010 | Al-Ali |
| 2010/0261979 A1 | 10/2010 | Kiani |
| 2010/0317936 A1 | 12/2010 | Al-Ali et al. |
| 2011/0001605 A1 | 1/2011 | Kiani et al. |
| 2011/0082711 A1 | 4/2011 | Poeze et al. |
| 2011/0105854 A1 | 5/2011 | Kiani et al. |
| 2011/0125060 A1 | 5/2011 | Telfort et al. |
| 2011/0172967 A1 | 7/2011 | Al-Ali et al. |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2011/0237969 A1 | 9/2011 | Eckerbom et al. |
| 2011/0288383 A1 | 11/2011 | Diab |
| 2012/0041316 A1 | 2/2012 | Al-Ali et al. |
| 2012/0046557 A1 | 2/2012 | Kiani |
| 2012/0059267 A1 | 3/2012 | Lamego et al. |
| 2012/0088984 A1 | 4/2012 | Al-Ali et al. |
| 2012/0116175 A1 | 5/2012 | Al-Ali et al. |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0265039 A1 | 10/2012 | Kiani |
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0302894 A1 | 11/2012 | Diab et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0045685 A1 | 2/2013 | Kiani |
| 2013/0046204 A1 | 2/2013 | Lamego et al. |
| 2013/0041591 A1 | 3/2013 | Lamego |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0267804 A1 | 10/2013 | Al-Ali |
| 2013/0274571 A1 | 10/2013 | Diab et al. |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0317327 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0324817 A1 | 12/2013 | Diab |
| 2013/0331660 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0022256 A1* | 1/2014 | Carnes ............... A61B 5/14553 345/440.1 |
| 2014/0025306 A1 | 1/2014 | Weber et al. |
| 2014/0031650 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0073167 A1 | 3/2014 | Al-Ali et al. |
| 2014/0077956 A1 | 3/2014 | Sampath et al. |
| 2014/0081097 A1 | 3/2014 | Al-Ali et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0155712 A1 | 6/2014 | Lamego et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0336481 A1 | 11/2014 | Shakespeare et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0080754 A1 | 3/2015 | Purdon et al. |

(56) References Cited

U.S. PATENT DOCUMENTS

| | | |
|---|---|---|
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Kind et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014084 A1 | 1/2017 | Al-Ali et al. |
| 2017/0021099 A1 | 1/2017 | Al-Ali et al. |
| 2017/0027456 A1 | 2/2017 | Kinast et al. |
| 2017/0042488 A1 | 2/2017 | Muhsin |
| 2017/0055847 A1 | 3/2017 | Kiani et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |

\* cited by examiner

REGIONAL OXIMETRY USER INTERFACE

PRIORITY CLAIM AND RELATED APPLICATIONS

Any and all applications for which a foreign or domestic priority claim is identified in the Application Data Sheet as filed with the present application are hereby incorporated by reference under 37 CFR 1.57.

This application claims a priority benefit under 35 U.S.C. § 119 to the following U.S. Provisional Patent Applications:

| Ser. No. | Date | Title |
|---|---|---|
| 61/887,856, | Oct. 7, 2013, | Regional Oximetry Sensor, |
| 61/887,878, | Oct. 7, 2013, | Regional Oximetry Pod, |
| 61/887,883 | Oct. 7, 2013, | Regional Oximetry User interface, and |
| 62/012,170 | Jun. 13, 2014 | Peel-Off Resistant Regional Oximetry Sensor |

Each of the foregoing disclosures is incorporated by reference herein in its entirety.

FIELD OF THE DISCLOSURE

The present disclosure relates generally to patient monitoring devices and systems, and specifically to improving user interaction with a patient monitor and medical data communication hub.

BACKGROUND OF THE DISCLOSURE

Regional oximetry, also referred to as tissue oximetry and cerebral oximetry, enables the continuous assessment of the oxygenation of tissue. The measurement is taken by placing one or more sensors on a patient, frequently on the patient's left and right forehead. Regional oximetry estimates regional tissue oxygenation by transcutaneous measurement of areas that are vulnerable to changes in oxygen supply and demand. Regional oximetry exploits the ability of light to penetrate tissue and determine hemoglobin oxygenation according to the amount of light absorbed by hemoglobin.

Regional oximetry differs from pulse oximetry in that tissue sampling represents primarily (70-75%) venous, and less (20-25%) arterial blood.

The technique uses two photo-detectors with each light source, thereby allowing selective sampling of tissue beyond a specified depth beneath the skin. Near-field photo-detection is subtracted from far-field photo-detection to provide selective tissue oxygenation measurement beyond a predefined depth. Moreover, regional oximetry monitoring does not depend upon pulsatile flow.

Regional oximetry is a useful patient monitoring technique to alert clinicians to dangerous clinical conditions. Changes in regional oximetry have been shown to occur in the absence of changes in arterial saturation or systemic hemodynamic parameters.

SUMMARY

The present disclosure provides a regional oximetry system with improved user interaction. In one aspect of the regional oximetry system, a display is provided, and a processor is provided causing a plurality of views to be displayed on the display. The views are configured to occupy at least a portion of the display. In some embodiments a first sensor port is configured to receive a first physiological signal representative of a regional tissue oxygenation level. In some embodiments a second sensor port is configured to receive a second physiological signal representative of an arterial oxygen saturation level. In some embodiments, the views are adapted to present data responsive to at least one physiological signal. In some embodiments, one view presents a first trend graph of a first physiological signal representative of a regional tissue oxygenation level, and a second trend graph of a second physiological signal representative of an arterial oxygen saturation level. In some embodiments an area between the first trend graph and the second trend graph can include a differential analysis of regional-to-central oxygen saturation.

Another aspect of a regional oximetry system includes obtaining a first waveform responsive to a physiological signal representative of a regional tissue oxygenation level, obtaining a second waveform responsive to a physiological signal representative of an arterial oxygen saturation level, determining, using at least one processor, a data trend responsive to the first physiological signal, determining, using at least one processor, a data trend responsive to the second physiological signal, and determining, using the at least one processor, a difference between the data trend responsive to the first physiological signal and the data trend responsive to the second physiological signal. In some embodiments, the regional oximetry system further presents, in a first display view, the determined data trends responsive to the first and second physiological signals, and in a second display view, the determined difference between the data trend responsive to the first and second physiological signals.

Yet another aspect of a regional oximetry system is a display and a processor causing a plurality of views to be displayed on the display. In some embodiments the views are configured to occupy at least a portion of the display. The views are adapted to present data responsive to at least one physiological signal. In some embodiments a first sensor port is configured to receive a first physiological signal representative of a regional tissue oxygenation level. In some embodiments the processor is configured to set a baseline level representative of an acceptable state of the regional tissue oxygenation. One view, for example, can present a differential analysis of a physiological signal representative of a regional tissue oxygenation level and a baseline level representative of an acceptable state of regional tissue oxygenation.

In yet another aspect of a regional oximetry system a display is provided, a sensor port is provided that is adapted to communicate with at least one sensor, and a processor is provided causing a plurality of views to be displayed on the display. The views are configured to occupy at least a portion of the display. A set sensor menu view is configured to occupy at least a portion of the display and is adapted to present a connectivity status of the sensor port and the at least one sensor.

For purposes of summarizing the disclosure, certain aspects, advantages, and novel features have been described herein. Of course, it is to be understood that not necessarily all such aspects, advantages, or features will be embodied in any particular embodiment.

BRIEF DESCRIPTION OF THE DRAWINGS

The following drawings and the associated descriptions are provided to illustrate embodiments of the present disclosure and do not limit the scope of the claims.

Figure 1A:
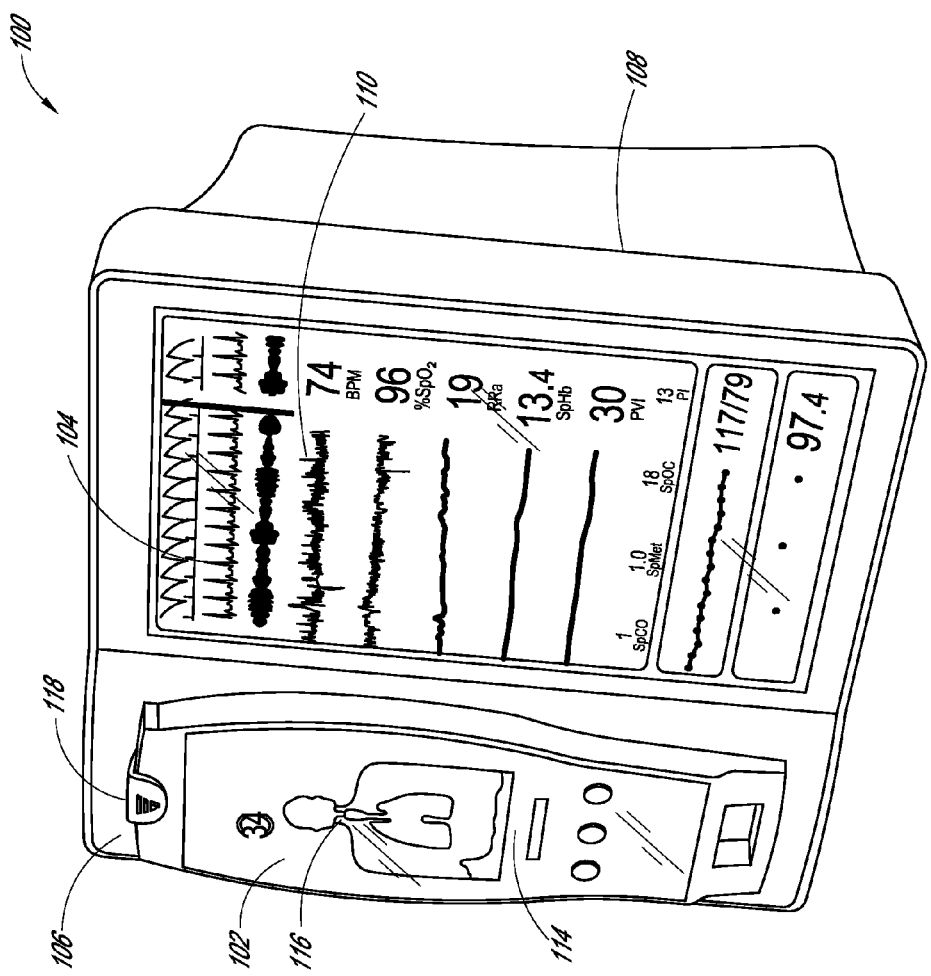
FIGS. 1A-1C are perspective views of a medical monitoring hub.

While the foregoing "Brief Description of the Drawings" references generally various embodiments of the disclosure, an artisan will recognize from the disclosure herein that such embodiments are not mutually exclusive. Rather, the artisan would recognize a myriad of combinations of some or all of such embodiments.

DETAILED DESCRIPTION

The following description is merely illustrative in nature and is in no way intended to limit the disclosure, its application, or uses. For purposes of clarity, the same reference numbers will be used in the drawings to identify similar elements. It should be understood that steps within a method may be executed in different order without altering the principles of the present disclosure.

The present disclosure relates to a user interface for a medical monitoring hub configured to be the center of monitoring activity for a given patient. An example of a medical monitoring hub is disclosed in U.S. patent application Ser. No. 13/651,167 assigned to the assignee of the present disclosure, and is incorporated by reference herein.

In an embodiment, the hub comprises a large, easily-readable display, such as an about ten (10) inch display dominating the majority of real estate on a front face of the hub. The display could be much larger or much smaller depending upon design constraints. However, for portability and current design goals, the preferred display is roughly sized proportional to the vertical footprint of one of the dockable portable patient monitors. Other considerations are recognizable by those skilled in the art from the disclosure herein.

The display provides measurement data for a wide variety of monitored parameters for the patient under observation in numerical or graphic form. In various embodiments, the measurement data is automatically configured based on the type of data and information being received at the hub. In an embodiment, the hub is moveable, portable, and mountable so that it can be positioned to convenient areas within a caregiver environment. For example, the hub is collected within a singular housing.

In an embodiment, the hub may advantageously receive data from a portable patient monitor while docked or undocked from the hub. Typical portable patient monitors, such as oximeters or co-oximeters can provide measurement data for a large number of physiological parameters derived from signals output from optical and/or acoustic sensors, electrodes, or the like. The physiological parameters include, but are not limited to oxygen saturation (including arterial blood oxygenation, regional oximetry (also known as tissue oximetry and cerebral oximetry), carboxyhemoglobin, methemoglobin, total hemoglobin, glucose, pH, bilirubin, fractional saturation, pulse rate, respiration rate, components of a respiration cycle, indications of perfusion including perfusion index, signal quality and/or confidences, plethysmograph data, indications of wellness or wellness indexes or other combinations of measurement data, audio information responsive to respiration, ailment identification or diagnosis, blood pressure, patient and/or measurement site temperature, depth of sedation, organ or brain oxygenation, hydration, measurements responsive to metabolism, combinations of the same or the like, to name a few. In other embodiments, the hub may output data sufficient to accomplish closed-loop drug administration in combination with infusion pumps or the like.

In an embodiment, the hub communicates with other devices that are interacting with the patient in a number of ways in a monitoring environment. For example, the hub advantageously receives serial data from other devices without necessitating their reprogramming or that of the hub. Such other devices include pumps, ventilators, all manner of monitors monitoring any combination of the foregoing parameters, ECG/EEG/EKG devices, electronic patient beds, and the like. Moreover, the hub advantageously receives channel data from other medical devices without necessitating their reprogramming or that of the hub. When a device communicates through channel data, the hub may advantageously alter the large display to include measurement information from that device. Additionally, the hub accesses call systems, such as those used by nurses or other attendants, to ensure that call situations from the device are passed to the appropriate nurse or attendant call system.

The hub also communicates with hospital systems to advantageously associate incoming patient measurement and treatment data with the patient being monitored. For example, the hub may communicate wirelessly or otherwise to a multi-patient monitoring system, such as a server or collection of servers, which in turn may communicate with a caregiver's data management systems, such as, for example, an Admit, Discharge, Transfer ("ADT") system and/or an Electronic Medical Records ("EMR") system. The hub advantageously associates the data flowing through it with the patient being monitored, thereby providing the electronic measurement and treatment information to be passed to the caregiver's data management systems without the caregiver associating each device in the environment with the patient.

In an embodiment, the hub advantageously includes a reconfigurable and removable docking station. The docking station may dock additional layered docking stations to adapt to different patient monitoring devices. Additionally, the docking station itself is modularized so that it may be removed if the primary dockable portable patient monitor changes its form factor. Thus, the hub is flexible in how its docking station is configured.

In an embodiment, the hub includes a large memory for storing some or all of the data it receives, processes, and/or associates with the patient, and/or communications it has with other devices and systems. Some or all of the memory may advantageously comprise removable SD memory.

The hub communicates with other devices through at least (1) the docking station to acquire data from a portable monitor, (2) innovative universal medical connectors to acquire channel data, (3) serial data connectors, such as RJ ports to acquire output data, (4) Ethernet, USB, and nurse call ports, (5) Wireless devices to acquire data from a portable monitor, and (6) other wired or wireless communication mechanisms known to an artisan. The universal medical connectors advantageously provide optional electrically-isolated power and communications, and are designed to be smaller in cross section than other commonly-used isolation configurations. The connectors and the hub communicate to advantageously translate or configure data from other devices to be usable and displayable for the hub. In an embodiment, a software developers kit ("SDK") is provided to a device manufacturer to establish or define the behavior and meaning of the data output from their device. When the output is defined, the definition is programmed into a memory residing in the cable side of the universal medical connector and supplied as an original equipment manufacturer ("OEM") to the device provider. When the cable is connected between the device and the hub, the hub understands the data and can use it for display and processing purposes without necessitating software upgrades to the device or the hub. In an embodiment, the hub can negotiate the schema and even add additional compression and/or encryption. Through the use of the universal medical connectors, the hub organizes the measurement and treatment data into a single display and alarm system effectively and efficiently, bringing order to the monitoring environment.

As the hub receives and tracks data from other devices according to a channel paradigm, the hub may advantageously provide processing to create virtual channels of patient measurement or treatment data. In an embodiment, a virtual channel may comprise a non-measured parameter that is, for example, the result of processing data from various measured or other parameters. An example of such a parameter includes a wellness indicator derived from various measured parameters that give an overall indication of the wellbeing of the monitored patient. An example of a wellness parameter is disclosed in U.S. patent application Ser. Nos. 13/269,296, 13/371,767 and 12/904,925, by the assignee of the present disclosure and incorporated by reference herein. By organizing data into channels and virtual channels, the hub may advantageously time-wise synchronize incoming data and virtual channel data.

The hub also receives serial data through serial communication ports, such as RJ connectors. The serial data is associated with the monitored patient and passed on to the multi-patient server systems and/or caregiver backend systems discussed above. Through receiving the serial data, the caregiver advantageously associates devices in the caregiver environment, often from varied manufacturers, with a particular patient, avoiding a need to have each individual device associated with the patient communicating independently with hospital systems. Such association is vital as it reduces caregiver time spent entering biographic and demographic information about the patient into each device. Moreover, in an embodiment, through the SDK the device manufacturer may advantageously provide information associated with any measurement delay of their device, thereby further allowing the hub to advantageously time-wise synchronize serial incoming data and other data associated with the patient.

In an embodiment, when a portable patient monitor is docked, and it includes its own display, the hub effectively increases its display real estate. For example, in an embodiment, the portable patient monitor may simply continue to display its measurement and/or treatment data, which may be now duplicated on the hub display, or the docked display may alter its display to provide additional information. In an embodiment, the docked display, when docked, presents anatomical graphical data of, for example, the heart, lungs, organs, the brain, or other body parts being measured and/or treated. The graphical data may advantageously animate similar to and in concert with the measurement data. For example, lungs may inflate in approximate correlation to the measured respiration rate and/or the determined inspiration/expiration portions of a respiration cycle; the heart may beat according to the pulse rate or along generally understood actual heart contraction patterns; the brain may change color or activity based on varying depths of sedation; or the like. In an embodiment, when the measured parameters indicate a need to alert a caregiver, a changing severity in color may be associated with one or more displayed graphics, such as the heart, lungs, brain, organs, circulatory system or portions thereof, respiratory system or portions thereof, other body parts or the like. In still other embodiments, the body portions may include animations on where, when or how to attach measurement devices.

The hub may also advantageously overlap parameter displays to provide additional visual information to the caregiver. Such overlapping may be user definable and configurable. The display may also incorporate analog-appearing icons or graphical indicia.

In the interest of clarity, not all features of an actual implementation are described in this specification. An artisan will of course appreciate that in the development of any such actual implementation (as in any development project), numerous implementation-specific decisions must be made to achieve a developer's specific goals and sub-goals, such as compliance with system and business-related constraints, which will vary from one implementation to another. Moreover, it will be appreciated that such a development effort might be complex and time-consuming, but would nevertheless be a routine undertaking of device and systems engineering for those of ordinary skill having the benefit of this disclosure.

To facilitate a complete understanding of the disclosure, the remainder of the detailed description describes the disclosure with reference to the drawings, wherein like reference numbers are referenced with like numerals throughout.

FIG. 1A illustrates a perspective view of an embodiment of a medical monitoring hub 100 with an embodiment of a docked portable patient monitor 102 according to an embodiment of the disclosure. The hub 100 includes a display 104, and a docking station 106, which in an embodiment is configured to mechanically and electrically mate with the portable patient monitor 102, each housed in a movable, mountable and portable housing 108. The housing 108 includes a generally upright inclined shape configured to rest on a horizontal flat surface, although the housing 108 can be affixed in a wide variety of positions and mountings and comprise a wide variety of shapes and sizes.

In an embodiment, the display 104 may present a wide variety of measurement and/or treatment data in numerical, graphical, waveform, or other display indicia 110. In an embodiment, the display 104 occupies much of a front face of the housing 108, although an artisan will appreciate the display 104 may comprise a tablet or tabletop horizontal configuration, a laptop-like configuration or the like. Other embodiments may include communicating display information and data to a table computer, smartphone, television, or any display system recognizable to an artisan. The upright inclined configuration of FIG. 1A presents display information to a caregiver in an easily viewable manner.

Figure 1B:
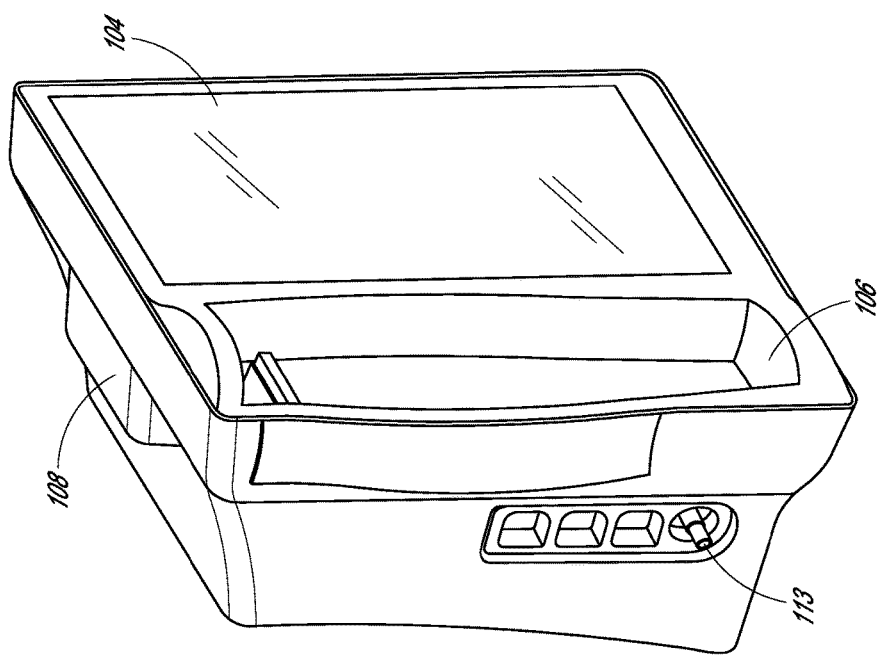

FIG. 1B shows a perspective side view of an embodiment of the hub 100 including the housing 108, the display 104, and the docking station 106 without a portable monitor docked. Also shown is a connector for noninvasive blood pressure (NIBP) 113.

Figure 1C:
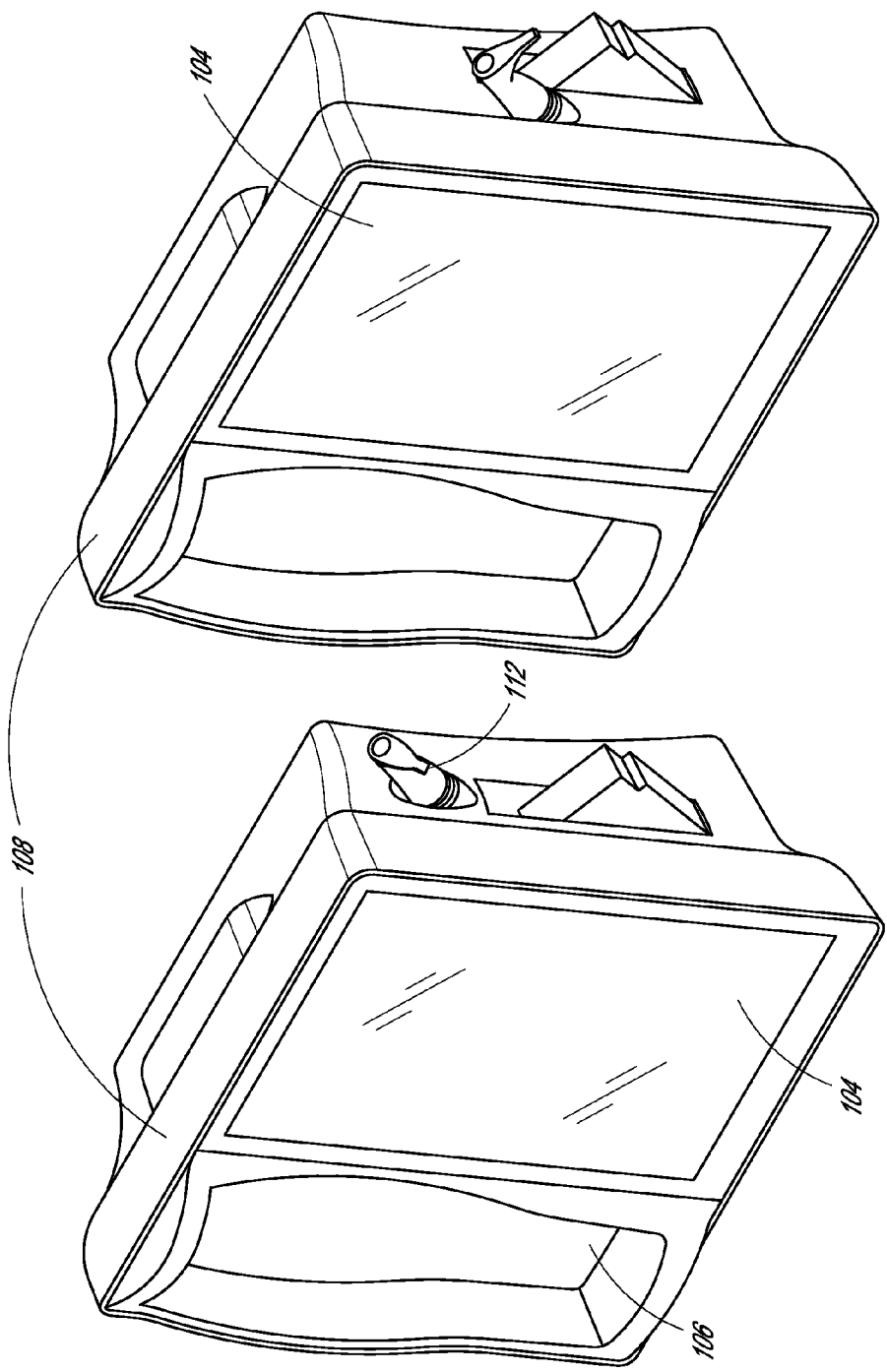

In an embodiment, the housing 108 may also include pockets or indentations to hold additional medical devices, such as, for example, a blood pressure monitor or temperature sensor 112, such as that shown in FIG. 1C.

The portable patient monitor 102 of FIG. 1A may advantageously comprise an oximeter, co-oximeter, respiratory monitor, depth of sedation monitor, noninvasive blood pressure monitor, vital signs monitor or the like, such as those commercially available from Masimo Corporation of Irvine, Calif., and/or disclosed in U.S. Pat. Pub. Nos. 2002/0140675, 2010/0274099, 2011/0213273, 2012/0226117, 2010/0030040; U.S. Pat. App. Ser. Nos. 61/242,792, 61/387457, 61/645,570, 13/554,908 and U.S. Pat. Nos. 6,157,850, 6,334,065, and the like. The portable patient monitor 102 may communicate with a variety of noninvasive and/or minimally invasive devices such as optical sensors with light emission and detection circuitry, acoustic sensors, devices that measure blood parameters from a finger prick, cuffs, ventilators, and the like. The portable patient monitor 102 may include its own display 114 presenting its own display indicia 116. The display indicia 116 may advantageously change based on a docking state of the portable patient monitor 102. When undocked, the display indicia 116 may include parameter information and may alter orientation based on information provided by, for example, a gravity sensor or an accelerometer.

In an embodiment, the docking station 106 of the hub 100 includes a mechanical latch 118, or a mechanically releasable catch to ensure that movement of the hub 100 doesn't mechanically detach the portable patient monitor 102 in a manner that could damage the same.

Although disclosed with reference to particular portable patient monitors 102, an artisan will recognize from the disclosure herein there is a large number and wide variety of medical devices that may advantageously dock with the hub 100. Moreover, the docking station 106 may advantageously electrically and not mechanically connect with the monitor 102, and/or wirelessly communicate with the same.

Figure 2:
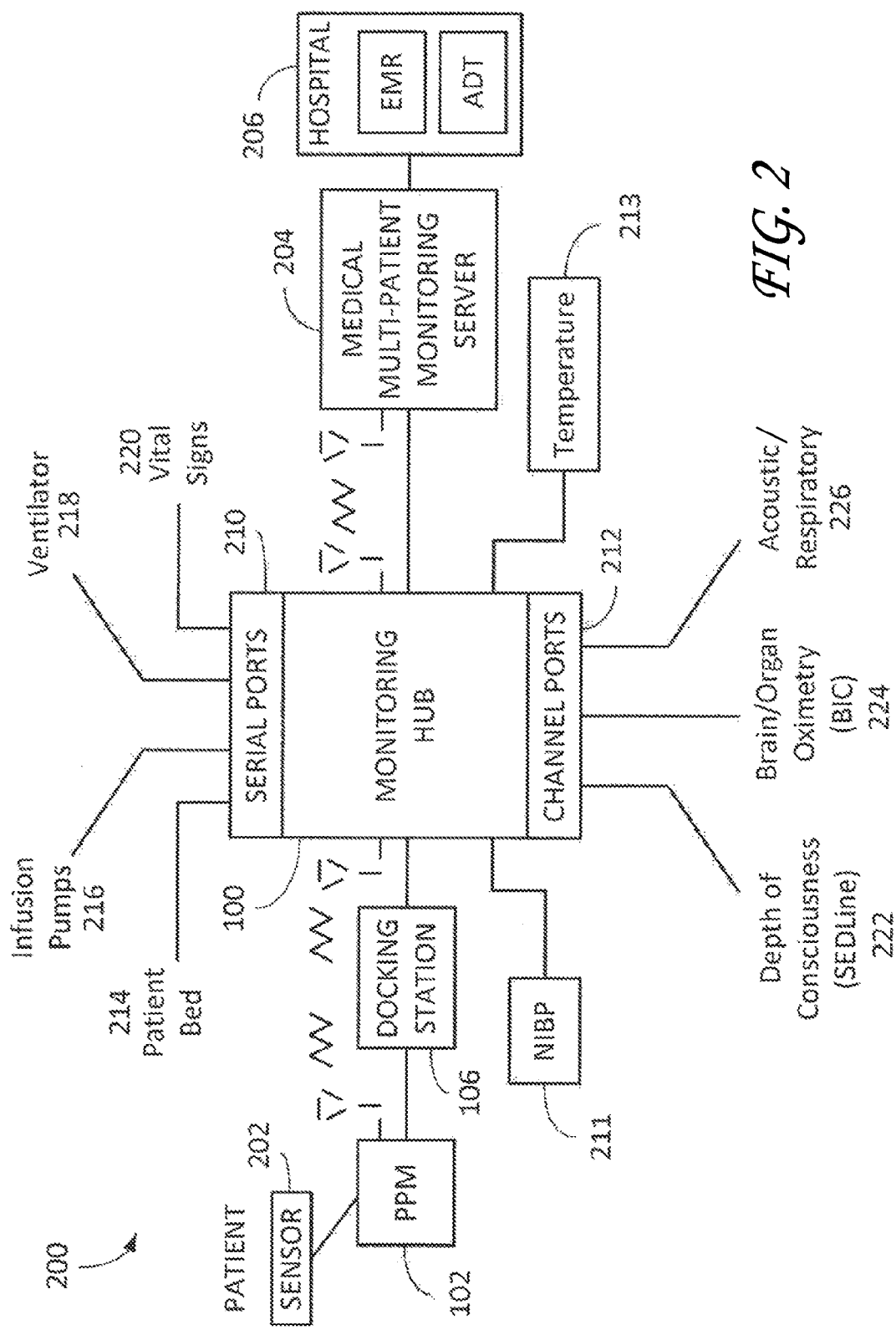
FIG. 2 is a simplified block diagram of a medical monitoring environment.

FIG. 2 illustrates a simplified block diagram of a monitoring environment 200 including the hub 100 of FIGS. 1A-1C, according to an embodiment of the disclosure. As shown in FIG. 2, the environment may include the portable patient monitor 102 communicating with one or more patient sensors 202, such as, for example, oximetry optical sensors, acoustic sensors, blood pressure sensors, respiration sensors or the like. In an embodiment, additional sensors, such as, for example, a NIBP sensor or system 211 and a temperature sensor or sensor system 213 may communicate directly with the hub 100. The sensors 202, 211 and 213 when in use are typically in proximity to the patient being monitored if not actually attached to the patient at a measurement site.

As disclosed, the portable patient monitor 102 communicates with the hub 100, in an embodiment, through the docking station 106 when docked and, in an embodiment, wirelessly when undocked, however, such undocked communication is not required. The hub 100 communicates with one or more multi-patient monitoring servers 204 or server systems, such as, for example, those disclosed with in U.S. Pat. Pub. Nos. 2011/0105854, 2011/0169644, and 2007/0180140. In general, the server 204 communicates with caregiver backend systems 206 such as EMR and/or ADT systems. The server 204 may advantageously obtain through push, pull or combination technologies patient information entered at patient admission, such as demographical information, billing information, and the like. The hub 100 accesses this information to seamlessly associate the monitored patient with the caregiver backend systems 206. Communication between the server 204 and the monitoring hub 100 may be accomplished by any technique recognizable to an artisan from the disclosure herein, including wireless, wired, over mobile or other computing networks, or the like.

FIG. 2 also shows the hub 100 communicating through its serial data ports 210 and channel data ports 212. As disclosed in the forgoing, the serial data ports 210 may provide data from a wide variety of patient medical devices, including electronic patient bed systems 214, infusion pump systems 216 including closed-loop control systems, ventilator systems 218, blood pressure or other vital sign measurement systems 220, or the like. Similarly, the channel data ports 212 may provide data from a wide variety of patient medical devices, including any of the foregoing, and other medical devices. For example, the channel data ports 212 may receive data from depth of consciousness monitors 222, such as those commercially available from Masimo Corporation of Irvine, Calif. under the SEDLine® and under the O$_3$™ Regional Oximetry for the Root™ Patient Monitoring and Connectivity Platform™ brand names, brain or other organ oximetry devices 224, noninvasive blood pressure or acoustic devices 226, or the like. In an embodiment, a device that is connected to the hub 100 through one or more of the channel data ports 212 may include board-in-cable ("BIC") solutions, where the processing algorithms and the signal processing devices that accomplish those algorithms are mounted to a board housed in a cable or cable connector, which in some embodiments has no additional display technologies. The BIC solution outputs its measured parameter data to the channel port 212 to be displayed on the display 104 of hub 100. In an embodiment, the hub 100 may advantageously be entirely or partially formed as a BIC solution that communicates with other systems, such as, for example, tablets, smartphones, or other computing systems.

Although illustrated with reference to a single docking station 106, the environment 200 may include multiple, stacked docking stations where a subsequent docking station mechanically and electrically docks to a first docking station to change the form factor for a different portable patent monitor. Such stacking may include more than 2 docking stations, and may reduce or increase the form factor for mechanical compliance with mating mechanical structures on a portable device.

Figure 3:
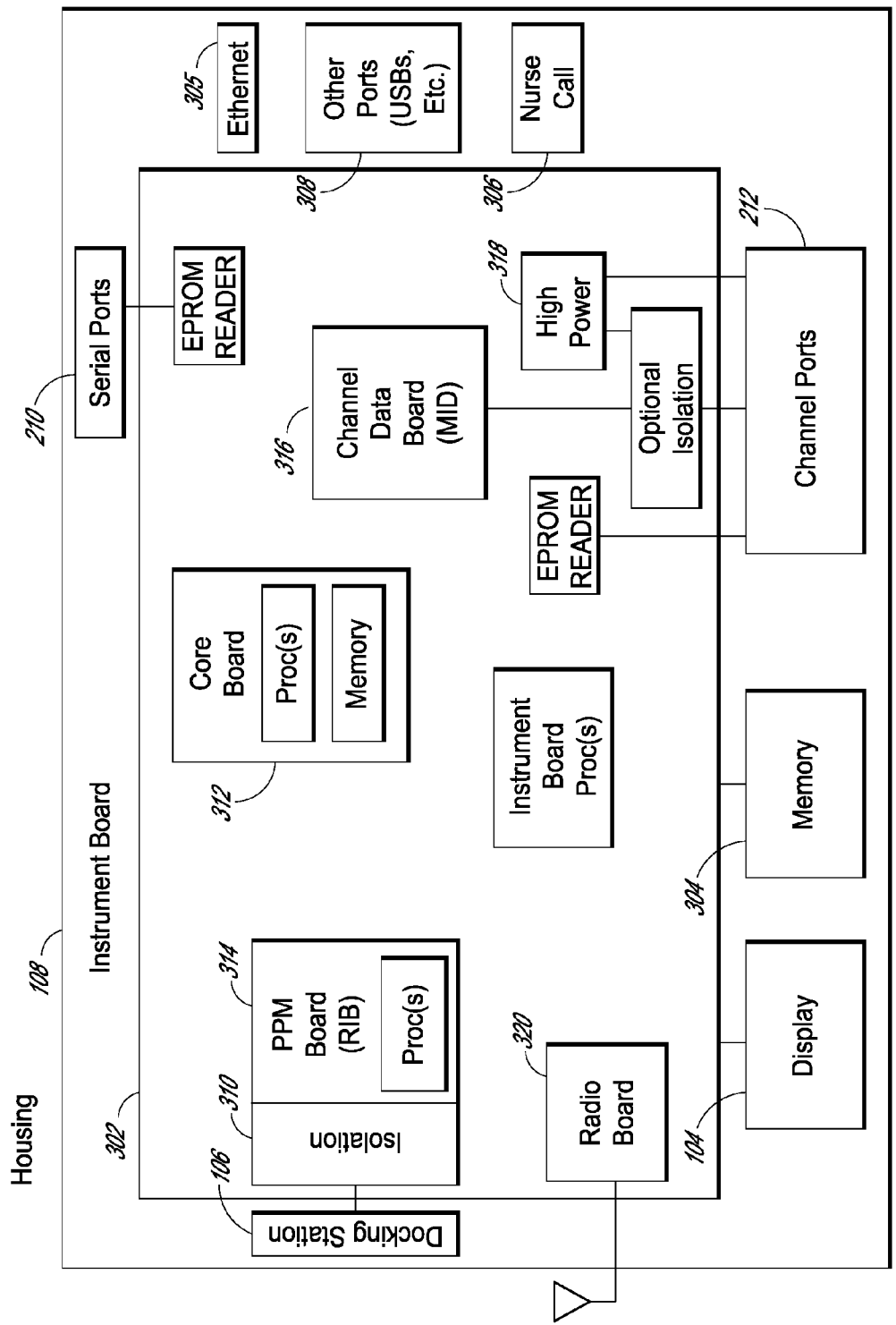
FIG. 3 is a simplified hardware block diagram of a medical monitoring system.

FIG. 3 illustrates a simplified hardware block diagram of the hub 100 of FIGS. 1A-1C, according to an embodiment of the disclosure. As shown in FIG. 3, the housing 108 of the hub 100 positions and/or encompasses an instrument board 302, the display 104, memory 304, and the various communication connections, including the serial ports 210, the channel ports 212, Ethernet ports 305, nurse call port 306, other communication ports 308 including standard USB or the like, and the docking station interface 310. The instrument board 302 comprises one or more substrates including communication interconnects, wiring, ports and the like to enable the communications and functions described herein, including inter-board communications. A core board 312 includes the main parameter, signal, and other processor(s) and memory. A portable patient monitor board ("RIB") 314 includes patient electrical isolation for the portable patient monitor 102 and one or more processors. A channel board ("MID") 316 controls the communication with the channel ports 212, including optional patient electrical isolation and power supply 318. A radio board 320 includes components configured for wireless communications. Additionally, the instrument board 302 may advantageously include one or more processors and controllers, busses, all manner of communication connectivity and electronics, memory, memory readers including EPROM readers, and other electronics recognizable to an artisan from the disclosure herein. Each board comprises substrates for positioning and support, interconnect for communications, electronic components including controllers, logic devices, hardware/software combinations and the like to accomplish the tasks designated above and others.

An artisan will recognize from the disclosure herein that the instrument board 302 may comprise a large number of electronic components organized in a large number of ways. Using different boards such as those disclosed above advantageously provides organization and compartmentalization to the complex system.

Attention is now directed to embodiments of a user interface by which a user may interact with the hub 100. In particular, a touchscreen display 104 is integral to the hub 100. An example of a physiological monitor touchscreen interface is disclosed in U.S. patent application Ser. No. 13/850,000, assigned to the assignee of the present disclosure, and is incorporated by reference herein.

In general, the touchscreen interface provides an intuitive, gesture-oriented control for the hub 100. The touchscreen interface employs interface constructs on the touchscreen display 104 that are particularly adapted to finger control gestures so as to change at least one of a physiological monitor operating characteristic and a physiological touchscreen display characteristic. In particular, the touchscreen display 104 presents a user with interface constructs responsive to finger control gestures so as to change displays and settings, such as monitor operating characteristics, display contents and display formats.

Figure 4:
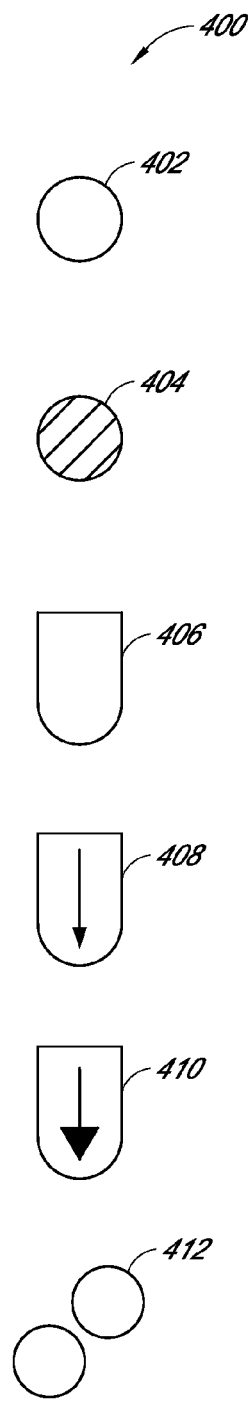
FIG. 4 is a finger control gesture legend for a touchscreen interface.

FIG. 4 illustrates a legend of finger control gestures 400 for use with a touchscreen display 104 according to an embodiment. The finger control gestures 400 include a touch 402, a touch and hold 404, a touch and move 406, a flick 408, a drag and drop 410, and a pinch 412. A touch 402 is a finger control gesture that executes the desired action once the user's finger is released from the screen. A touch and hold 404 is a finger control gesture that executes the desired action once the user has held his or her finger on the screen continuously for a predetermined duration (e.g., a few seconds), received a "hold completion" notification, and has released his or her finger from the screen. A touch and move 406 is a finger control gesture that manipulates and/or translates objects across the display 104 in the desired and permitted direction to a deliberate stopping point. To execute a touch and move finger control gesture 406, the user touches an object, moves the object (left, right, up, down, diagonally, etc.), and releases the object. A flick 408 is a finger control gesture comprising contact of an object on the display 104 in conjunction with a quick finger movement in a particular direction, typically along a single vector. To execute a flick 408 finger control gesture the user touches an object on the display 104, moves the object (typically, but not necessarily in a single direction) and releases the finger from the display 104 quickly, in a manner such that the contact point has a velocity throughout its path of motion. A drag and drop 410 is a finger control gesture by which the user moves an object to another location or to another object (e.g., a folder) and positions it there by releasing it. To execute a drag and drop 410 finger control gesture, the user touches, holds, drags and drops the object. A pinch 412 is a finger control gesture that expands or contracts the field of view on the display 104. To execute a pinch 412 finger control gesture, the user touches the display 104 at two touch points using two fingers, for example, the thumb and index finger of a user's hand. Moving the touch points apart from each other zooms in on the field of view, enlarging it, while moving the touch points together zooms out on the field of view, contracting it.

In an embodiment the user interface includes multiple controls. For example, a toggle control enables a user to slide a knob to switch between toggle states. The toggle control also enables the user to press left or right of the toggle to quickly move the toggle left or right. If the toggle control is labeled, the user can press the label to quickly move the knob left or right.

The following paragraphs include a description of additional touch screen controls that can be used with the system of the present disclosure. The system can include any combination of the following controls and the present disclosure is not intended to be limited by the following descriptions of various controls.

In some embodiments, a spinner control enables the user to press a center (focused) tile to expand a spinner when the spinner is closed and to collapse a spinner when the spinner is opened. The spinner control enables the user to swipe up or down which, when the spinner is open, scrolls through spinner tiles. The spinner control enables the user to press an unfocused tile which then scrolls the tile into a center, focused position. And the spinner control enables the user to collapse an open spinner by pressing anywhere outside the spinner.

A slider control enables the user to move a knob by sliding the knob. The slider control also enables the user to quickly move the knob to a specific position by pressing anywhere along the slider path.

A slider spinner control combines the control capabilities of the spinner control and the slider control.

A button control enables a user to perform an action, as defined by the button description, by pressing the button.

An icon menu control enables the user to open a specified menu by pressing a tile. The icon menu control enables the user to scroll icons left or right by swiping left or right anywhere on the display. The icon menu control enables the user to quickly center a tile corresponding to an indicator icon by pressing an indicator button.

A window control enables the user to open a parameter or measurement window when no parameter or measurement alarm is present, by pressing the parameter or measurement. The window control enables the user to silence a parameter or measurement alarm when a parameter or measurement alarm is present, by pressing the parameter or measurement. The window control enables a parameter or measurement to be moved to a different location on the display 104 by using a drag and drop 410 finger control gesture.

A well control enables the user to open a parameter or measurement menu when no parameter or measurement alarm is present, by pressing the parameter or measurement. The well control enables the user to silence a parameter or measurement alarm when a parameter or measurement alarm is present, by pressing the parameter or measurement.

A live waveform control enables the user to separate waveforms by swiping down. The live waveform control enables the user to combine waveforms by swiping up.

A trend line control enables the user to zoom in by pinching in, zoom out by pinching out, change a time range by panning, and open a parameter or measurement trend menu by pressing the y-axis.

An alarm silence icon control enables the user to silence all alarms by pressing the alarm silence icon.

An audio pause icon control enables the user to pause audio for a predetermined period of time, by pressing the audio pause icon.

Other status bar icon controls enable the user to open the relevant menu, by pressing the relevant status bar icon.

A back arrow control enables the user to exit a menu or abandon any changes made, by pressing a back arrow icon.

A confirm-or-cancel control enables the user to confirm changes to settings by pressing an OK button. The confirm-or-cancel control enables the user to cancel changes to settings by pressing a cancel button.

A home control enables the user to navigate to the main screen at any time by pressing a home button.

Figure 5:
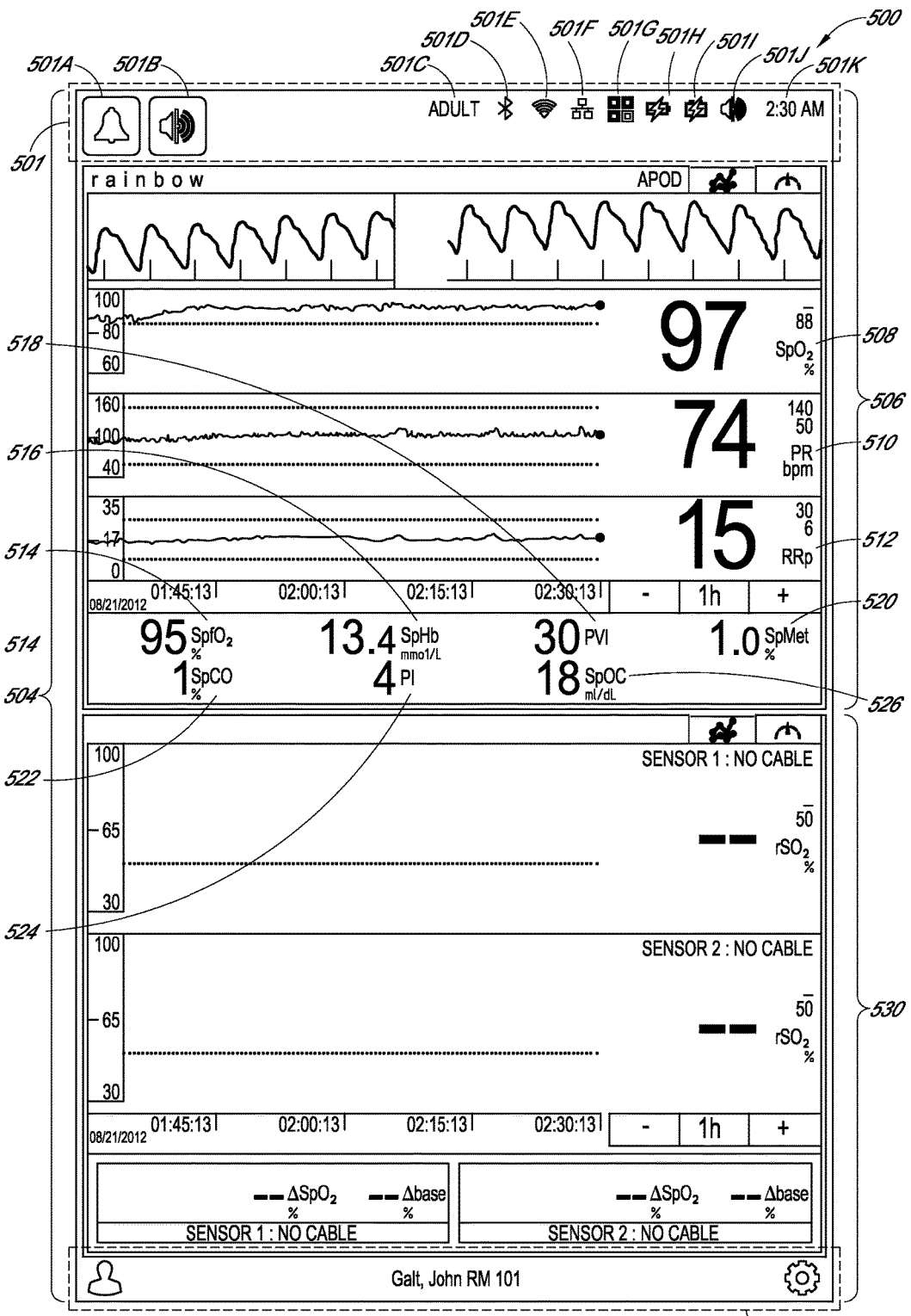
FIG. 5 is an illustration of a display view.

FIG. 5 illustrates an embodiment of a user interface 500 displayed on the display 104 of the hub 100. In an embodiment the display 104 comprises a color, modular, touch-screen integral to the hub 100. Positioned horizontally along the top of the display 104 is a top status line 501 that displays system status as well as that provide shortcuts to menu items or actions. In an embodiment the icons presented on the top status line 501 include alarm silence 501A, audio pause 501B, profiles 501C, Bluetooth 501D, Wi-Fi 501E, Ethernet 501F, connectivity gateway 501G, portable patient monitor battery status 501H, monitoring hub battery status 501I, sounds 501J, and current time 501K. The alarm silence icon 501A displays alarm status and mutes all audible alarms for monitoring devices connected to the hub 100. The audio pause icon 501B displays audio pause status and temporarily silences an alarm event. The profiles icon 501C provides access to a profiles screen; the example shown illustrates that the profile is set to "Adult" for an adult patient. The Bluetooth icon 501D provides access to a Bluetooth screen. If this icon is visible on the status line 501, then Bluetooth connectivity has been enabled. The Wi-Fi icon 501E provides access to a Wi-Fi screen. If this icon is visible on the status line 501, then Wi-Fi connectivity has been enabled. The icon itself also indicates the strength of the wireless signal. The Ethernet icon 501 F provides access to an Ethernet screen. If this icon is visible on the status line 501, then Ethernet connectivity has been enabled. The connectivity gateway icon 501G provides access to a connectivity gateway screen. The example illustrated indicates that stand-alone devices are connected to three of the available four ports. The color of the icon matches the status colors of the connected standalone devices. The portable patient monitor battery status icon 501H displays the charging status of the portable patient monitor 102 and provides access to a portable patient monitor battery screen. The example illustrates that the battery is currently charging. The monitoring hub battery status icon 501I displays the charging status of the monitoring hub 100 and provides access to a monitoring hub battery screen. The example illustrates that the battery is currently charging. The sounds icon 501J provides access to a sounds screen to adjust alarm and pulse tone volume. In an embodiment the sounds icon 501J does not indicate the actual volume level of the alarm and the pulse tone. The current time icon 501K displays the current time and provides access to a localization screen which contains settings related to local time, language and geography.

Positioned horizontally along the bottom of the display 104 is a bottom status line 502 that displays additional icons and information including a main menu icon, a gender icon, and a patient identifier that includes patient-specific information, such as, for example, the patient's name and room location. Although the disclosed embodiment employs status lines 501, 502 oriented horizontally along the top and bottom of the display 104, one skilled in the art would readily appreciate that information of the type presented in the top status line 501 and in the bottom status line 502 may be presented in numerous different formats, combinations and configurations, including without limitation, one or more status bars positioned vertically on the display 104. Moreover a skilled artisan will appreciate that other useful information may be displayed in status bars 501, 502.

In an embodiment the user interface creates a window for every monitoring device connected to the hub 100. Parameters or measurements can be expanded within a window to customize views. A central portion 504 of the display 104 presents patient measurement data, in this example, in two windows 506, 530. An upper window 506 presents patient data measured by an a noninvasive monitoring platform—such as the rainbow® Pulse CO-Oximetry™ monitoring platform by Masimo Corporation of Irvine, Calif.—which enables the assessment of multiple blood constituents and physiologic parameters including oxygen saturation ($SpO_2$) 508, pulse rate (PR) 510, respiration rate (RRp) 512, fractional arterial oxygen saturation ($SpfO_2$) 514, total hemoglobin (SpHb) 516, plethysmograph variability index (PVI) 518, methemoglobin (SpMet) 520, carboxyhemoglobin (SpCO) 522, perfusion index (PI) 524, and oxygen content (SpOC) 526.

Advantageously, the display 104 is configurable to permit the user to adjust the manner by which the physiologic parameters are presented on the display 104. In particular, physiologic measurements of greater interest or importance to the clinician may be displayed in larger format and may also be displayed in both numerical and graphical formats to convey the current measurement as well as the historical trend of measurements for a period of time, such as, for example, the preceding hour. In an embodiment the oxygen saturation 508, pulse rate 510, and respiration rate 512 measurements are displayed in such a manner, taking up a larger portion of the upper portion 506 of the display 104, while the fractional arterial oxygen saturation 514, total hemoglobin 516, plethysmograph variability index 518, methemoglobin 520, carboxyhemoglobin 522, perfusion index 524, and oxygen content 526 measurements are displayed as numbers, taking up a smaller portion of the upper portion 506 of the display 104.

In an embodiment the presentation of measurement information may be adjusted easily by using the finger control gestures 400. For example, the touch and move 406 finger control gesture may be used to move an object on the display 104 representing a measurement from one location of the display 104 to another location of the display 104. Advantageously, when the object is moved, the display 104 automatically scales its presentation of information based upon the parameters that are active. For example, fewer parameters result in the presentation of larger digits, trend lines, and waveform cycles. In an embodiment the location to which an object is moved determines, at least in part, the manner by which that object will be presented on the display 104.

A lower window 530 of the display 104 presents patient data measured by a regional oximetry platform—such as the $O_3$™ regional oximetry module by Masimo Corporation of Irvine, Calif.—which allows the continuous assessment of tissue oxygenation beneath one or more sensors placed on the patient's skin to help clinicians detect regional hypoxemia. Regional oximetry—also referred to as tissue oximetry and cerebral oximetry—enables the continuous assessment of the oxygenation of tissue beneath the sensor. Simultaneous measurement of both tissue oxygen saturation ($rSO_2$) and arterial blood oxygenation ($SpO_2$) provides clinicians, such as anesthesiologists or perfusionists, a differential analysis of regional-to-central oxygen saturation monitoring, which helps the clinician to maintain brain oxygenation and safe cerebral perfusion during procedures.

In an embodiment the regional oximetry module is configured by applying one or more regional oximetry sensors to the patient, for example, the patient's forehead, and by connecting the module(s) to the hub 100. In an embodiment the regional oximetry module has as few as one and as many as four sensors. In an embodiment the regional oximetry module is connected to the hub 100 through the hub's 100 channel ports 212.

In an embodiment the regional oximetry platform uses near-infrared spectroscopy (NIRS) to continuously and simultaneously measure regional oxygen saturation ($rSO_2$) and arterial oxygen saturation ($SpO_2$), enabling the regional oximetry platform to automatically derive the differential analysis of a patient's regional-to-central oxygen saturation. In an embodiment the hub 100 derives the differential analysis of a patient's regional-to-central oxygenation saturation by comparing measurements provided to the hub 100 from two sources, such as a pulse oximetry measurement device and a regional oximetry measurement device.

Figure 6:
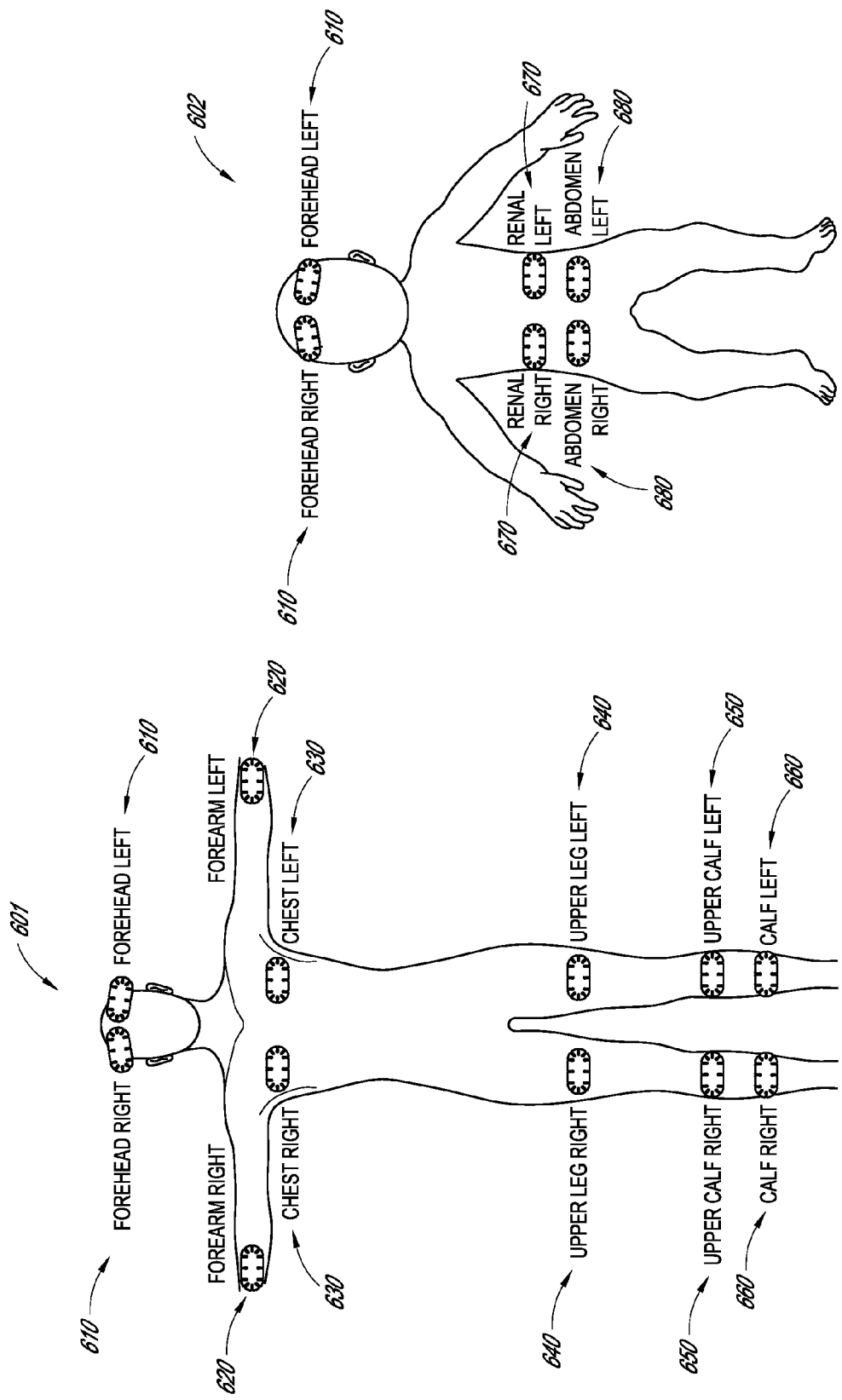
FIGS. 6A-6B are illustrations of potential regional oximetry sensor site locations for an adult and for a child, respectively.

FIGS. 6A-6B illustrate regional oximetry monitor user interface embodiments for designating adult and child sensor placement sites. As shown in FIG. 6A, an adult form 601 is generated on a user interface display. In an embodiment, between one and four sensor sites can be designated on the adult form 601, including left and right forehead 610, left and right forearm 620, left and right chest 630, left and right upper leg 640, left and right upper calf 650 and left and right calf 660 sites. Accordingly, between one and four sensors can be located on various combinations of these sites. The hub 100, which is in communication with these sensors, displays between one and four corresponding regional oximetry graphs and readouts, as described with respect to FIGS. 7 and 8, below. In other embodiments, any number of sensors and sensor sites can be used, including all of the sensor sites illustrated in FIG. 6A and/or other sensor sites as well.

As shown in FIG. 6B, a child form 602 is generated on a user interface display. In an embodiment between one and four sensor sites can be designated on the child form 602, including left and right forehead 610, left and right renal 670, and left and right abdomen 680 sites. Accordingly, between one and four sensors can be located on these sites. The hub 100, which is in communication with these sensors, displays between one and four corresponding regional oximetry graphs and readouts, as described in FIGS. 7 and 8 bellow. In other embodiments, any number of sensors and sensor sites can be used, including all of the sensor sites illustrated in FIG. 6B and/or other sensor sites as well.

Figure 7:
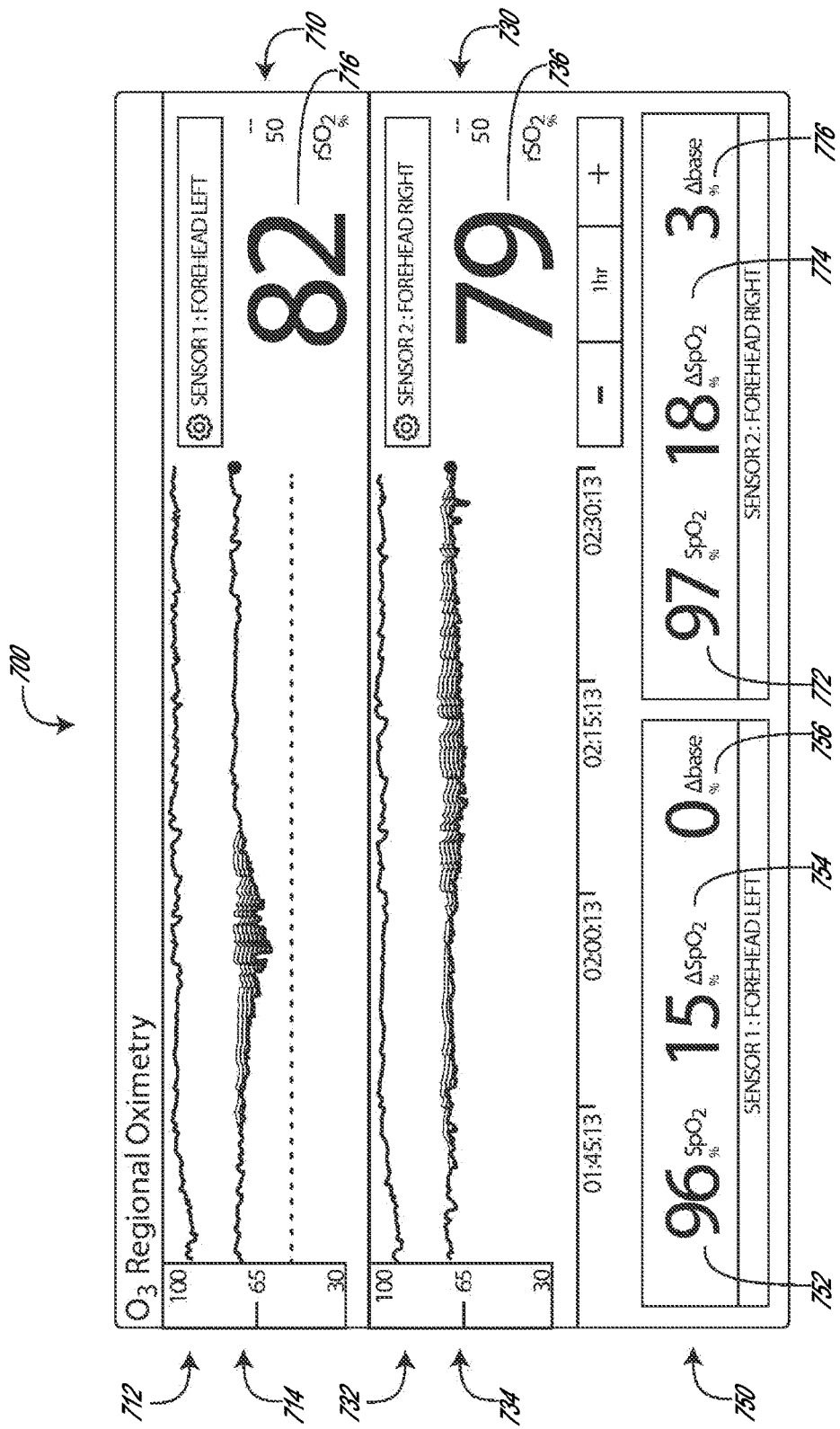
FIG. 7 is an illustration of a regional oximetry display.

FIG. 7 illustrates an embodiment of a regional oximetry window display 700 for monitoring parameters derived from one or more regional oximetry sensors. This particular example is a two-sensor display for monitoring, for example, a forehead left 710 site and a forehead right 730 site. In an upper portion of the display 700, the forehead left 710 site displays, for example, an $SpO_2$ graph 712, an $rSO_2$ graph 714 and an $rSO_2$ readout 716. Similarly, the forehead right 730 site displays, for example, an $SpO_2$ graph 732, an $rSO_2$ graph 734 and an $rSO_2$ readout 736. In other embodiments, any number of sensors and sensor sites can be used.

Also shown in FIG. 7, in a lower portion of the display 700, is a forehead left display well 750 that displays, for example, an $SpO_2$ readout 752, a $\Delta SpO_2$ readout 754 and a $\Delta$base readout 756. Similarly, the forehead right display well 730 displays, for example, an $SpO_2$ readout 772, a $\Delta SO_2$ readout 774 and a $\Delta$base readout 776.

Figure 8:
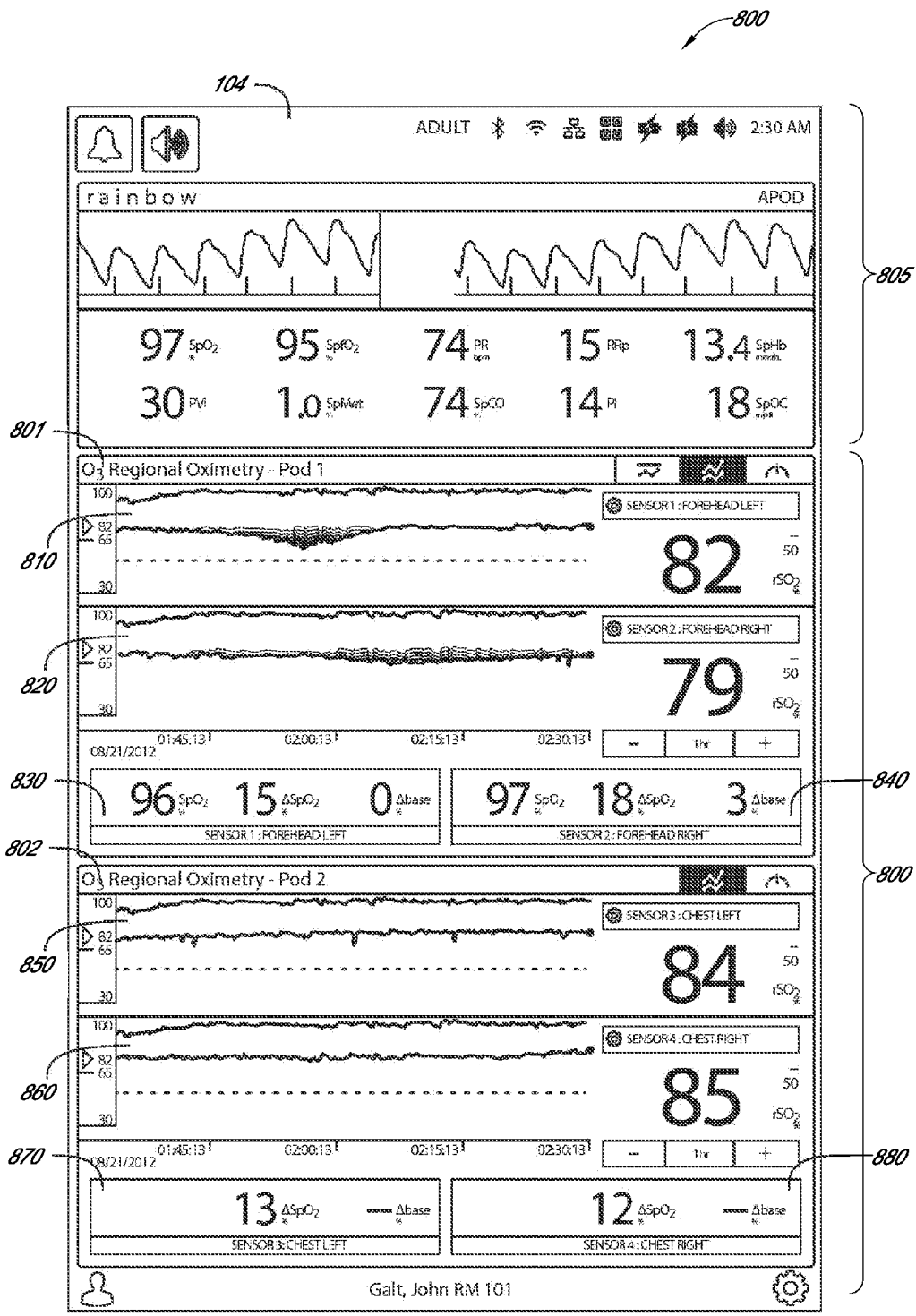
FIG. 8 is an illustration of a medical monitoring hub display.

FIG. 8 illustrates an embodiment of the user interface 800 in which a regional oximetry parameter display 104 accommodates four regional oximetry sensor inputs. In this example, a first two-sensor display 801 is enabled for monitoring a forehead left site 810, 830 and a forehead right site 820, 840. A second two-sensor display 802 is enabled for monitoring a chest left site 850, 870, and a chest right site 860, 880. Notably, a pulse oximetry parameter display 805 is allocated less display space than the regional oximetry parameter display 806 to accommodate the graphical area needed to display the regional oximetry parameter data. In an embodiment the display 800 automatically scales to allocate display space according to preferences set by the user. In other embodiments, any number of sensors and sensor sites can be used.

Figure 9A:
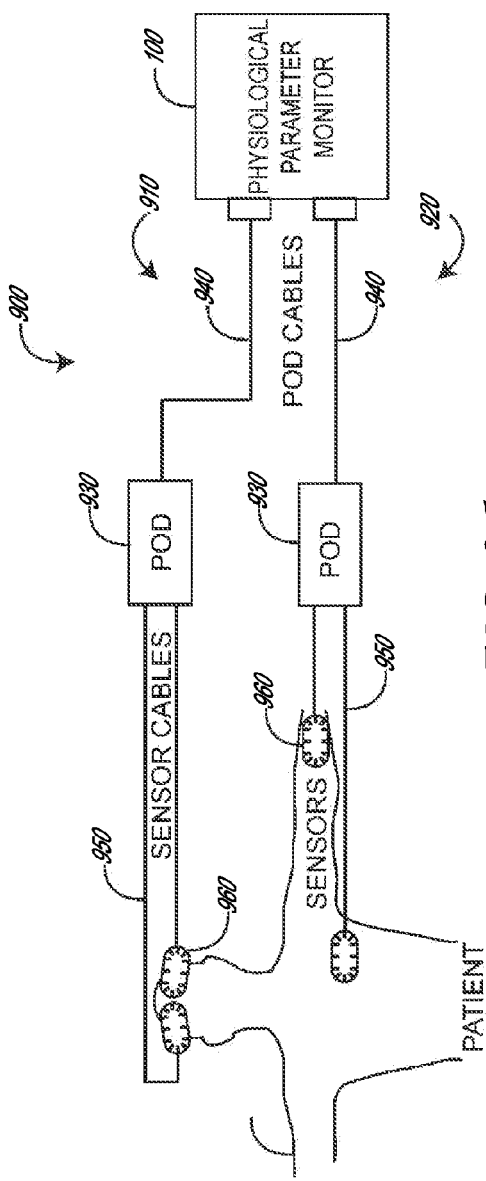
FIGS. 9A-9B illustrate embodiments for regional oximetry monitoring.
Figure 9B:
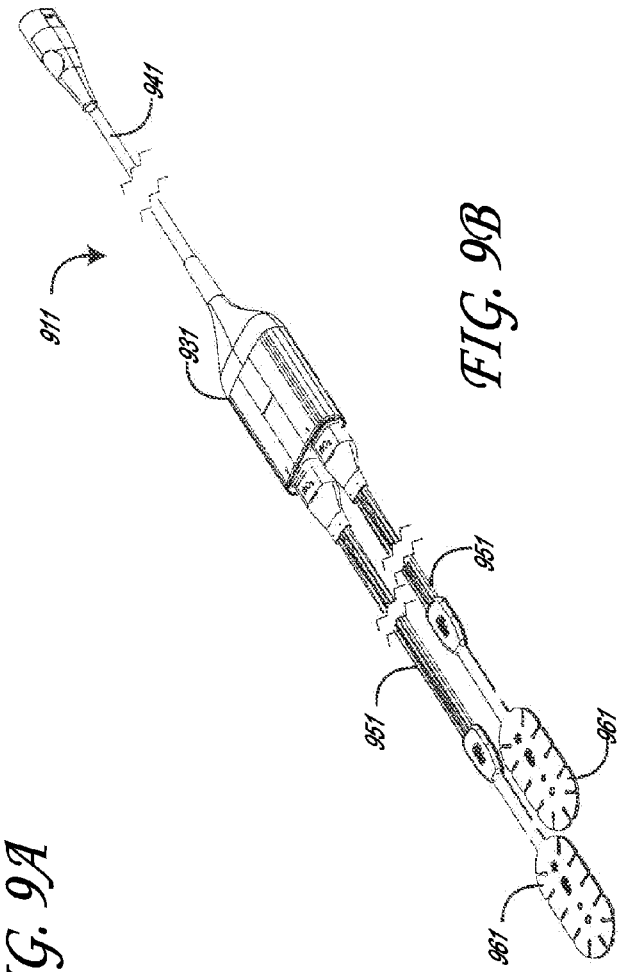

FIGS. 9A-9B generally illustrate embodiments for regional oximetry monitoring. As shown in FIG. 9A, a regional oximetry pod array 900 has a first pod assembly 910 and a second pod assembly 920. Each pod assembly 910, 920 communicates with an array of one or two regional oximetry sensors 960 via sensor cables 950. In other embodiments the pod assemblies 910, 920 can communicate with any number of regional oximetry sensors 960. The sensors 960 are attached to various patient locations, with one or two regional oximetry pods 930 and a corresponding number of pod cables 940 providing communications between the pods 930 and the hub 100. In other embodiments any number of sensors, positioned at any number of sensor sites on the patient's body can be used, and any number of pod assemblies can be used to connect the sensors to the hub 100. The pods 930 perform the physiological sensor signal processing normally associated with a monitoring device, which advantageously allows regional oximetry pods 930 to easily integrate with third party monitors 100 ranging from relatively "dumb" display devices that perform little or no signal processing to relatively "intelligent" multi-parameter patient monitors, which communicate with a variety of sensors and which perform sophisticated signal processing at the monitor level.

As shown in FIG. 9B, a regional oximetry pod assembly 911 embodiment has a pod 931 that communicates with up to two regional oximetry sensors 961 via sensor cables 951. In other embodiments the pod 931 can communicate with any number of regional oximetry sensors 961. In turn, the pod 931 communicates with an attached monitor hub 100 via a pod cable 941. In an embodiment the pod cable 941 connects to one of the channel ports 212 of the hub 100.

Embodiments of user interfaces for configuring a regional oximetry system to operate with a hub 100 follow.

When multiple regional oximetry sensors 960 are positioned on a patient's body and connected to the hub 100, there is a potential for confusion as to where each sensor is positioned on the patient. This potential for confusion is increased when, as in some embodiments, pod assemblies 920, 930 are used to connect multiple sensors 960 to the hub 100 because embodiments of pod assemblies 920, 930 can connect multiple sensors 960 to a single channel port 212 of the hub 100. Inadvertent mislabeling of sensor location can lead to misreading of the physiological data being displayed, thereby posing a risk to the patient. Advantageously embodiments of the user interface for configuring a regional oximetry system to operate with a hub 100, disclosed herein, address this concern by displaying information describing the connectivity status and configuration of sensors 960, pod assemblies 920, 930 and channel ports 212. In some embodiments the information describing the connectivity status and configuration includes visual representations to assist clinicians in properly labeling and configuring the hub 100 to work appropriately with a regional oximetry system.

Figure 10A:
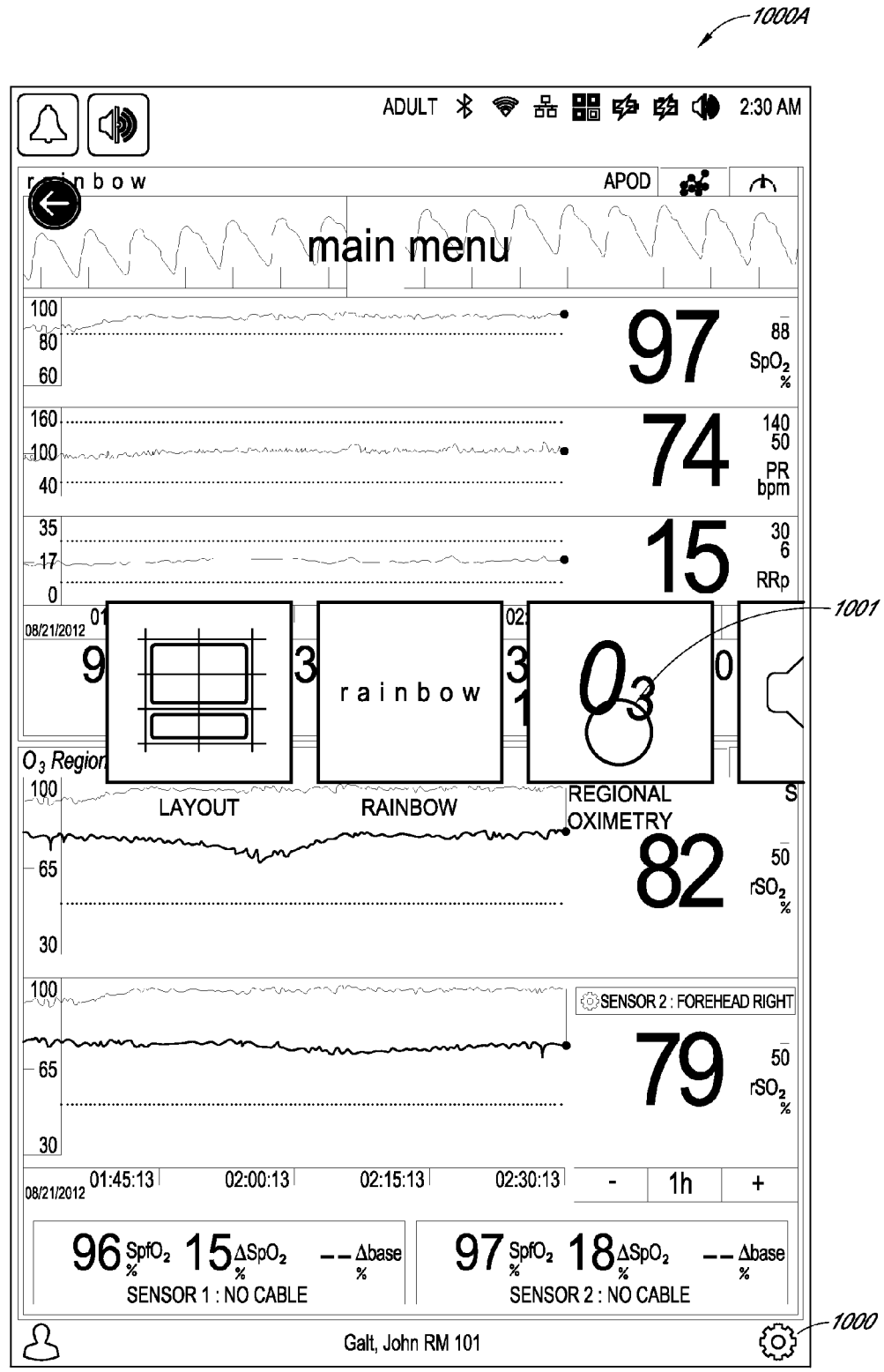
FIGS. 10A-10F illustrate embodiments of a user interface for selecting a regional oximetry sensor site.
Figure 10B:
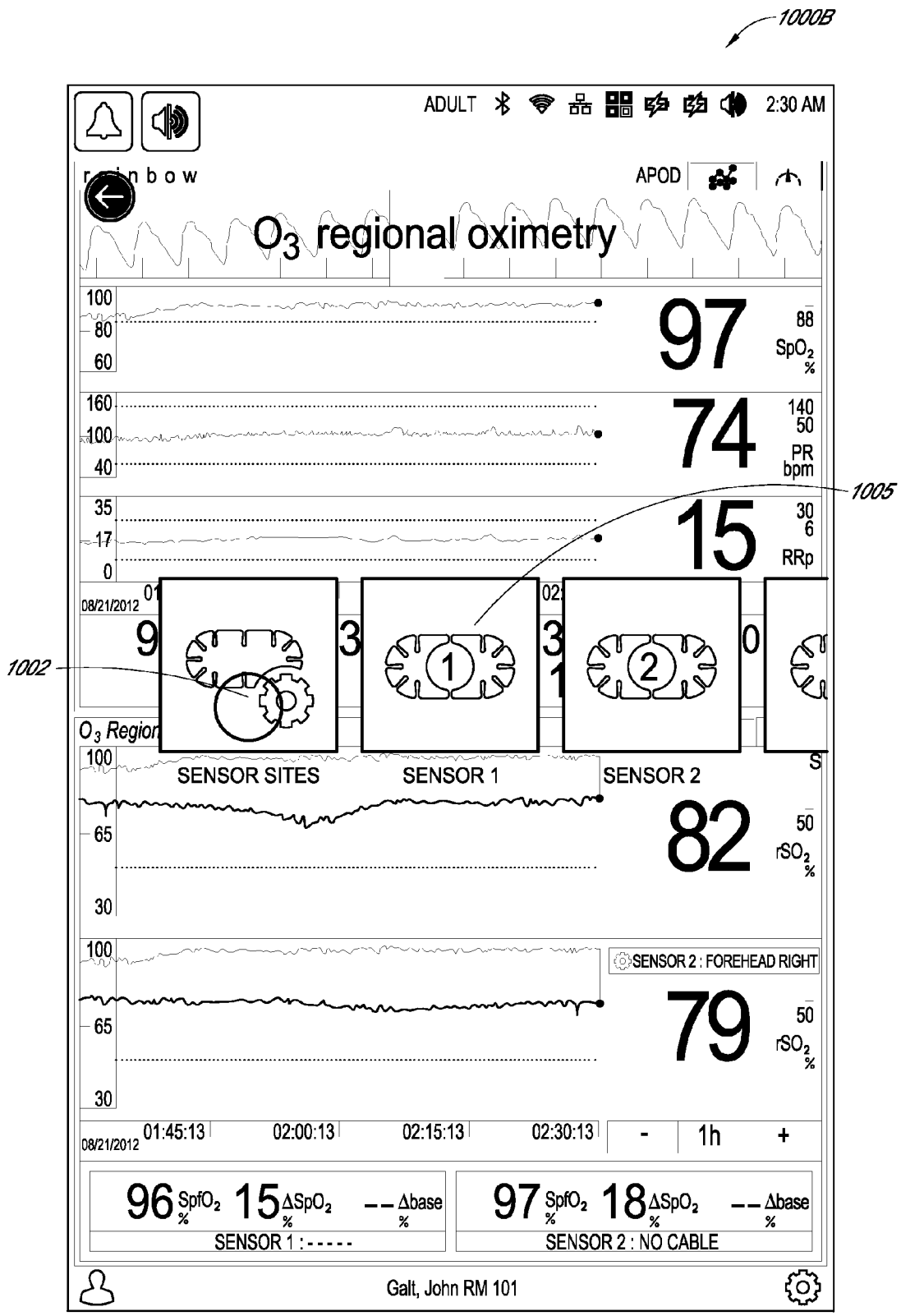
Figure 10C:
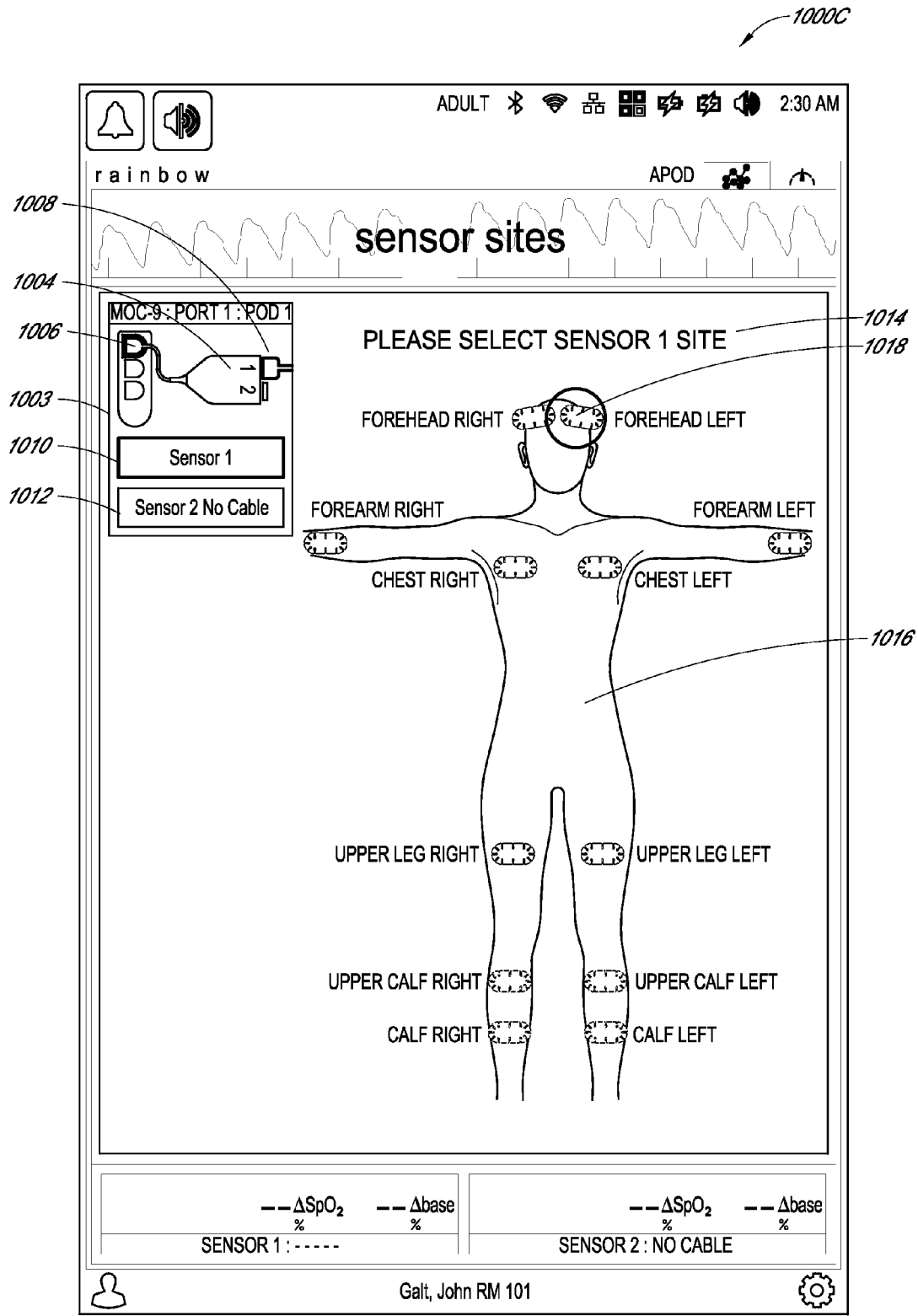

FIGS. 10A-10F illustrate embodiments of a user interface for selecting a first sensor site employing a menu-based, hierarchical navigation structure. FIG. 10A illustrates a main menu 1000A which is accessed by pressing a main menu icon 1000. The main menu presents several options for the user to select. The main menu options permit the user to navigate to various features of the user interface. Main menu options include, without limitation, device settings, information, trend settings, profiles, connectivity, layout, and sounds. As depicted in FIG. 10A, a regional oximetry device icon 1001 is selected using a touch 402 finger control gesture, which causes the display 104 to replace the main menu with a regional oximetry menu 1000B, illustrated in FIG. 10B. Selection of the sensor sites icon 1002 opens a sensor sites menu 1000C shown in FIG. 10C. As illustrated in FIG. 10C a connectivity window 1003 graphically displays the connectivity state of the channel ports 212 of the hub 100. In this illustrative example, pod 1 1004 is connected to port 1 1006, and sensor cable 1 1008 is connected to pod 1 1004. A sensor 1 button 1010 is illuminated to indicate that sensor 1 is connected. In contrast, a sensor 2 button 1012 is not illuminated (or grayed-out), indicating that no sensor cable is connected to it. An information line 1014 instructs the user to select a sensor 1 site. As illustrated, an adult form 1016 is generated to display potential sites of the patient's body where a regional oximetry sensor can be placed, including right and left forehead, right and left forearm, right and left chest, right and left upper leg, right and left upper calf, and right and left calf. With the touch finger control gesture 402 the user selects a sensor location on the adult form 1016 to identify where, on the patient, the regional oximetry sensor has been placed. As illustrated in FIG. 10O the left forehead sensor site 1018 is selected.

Figure 10D:
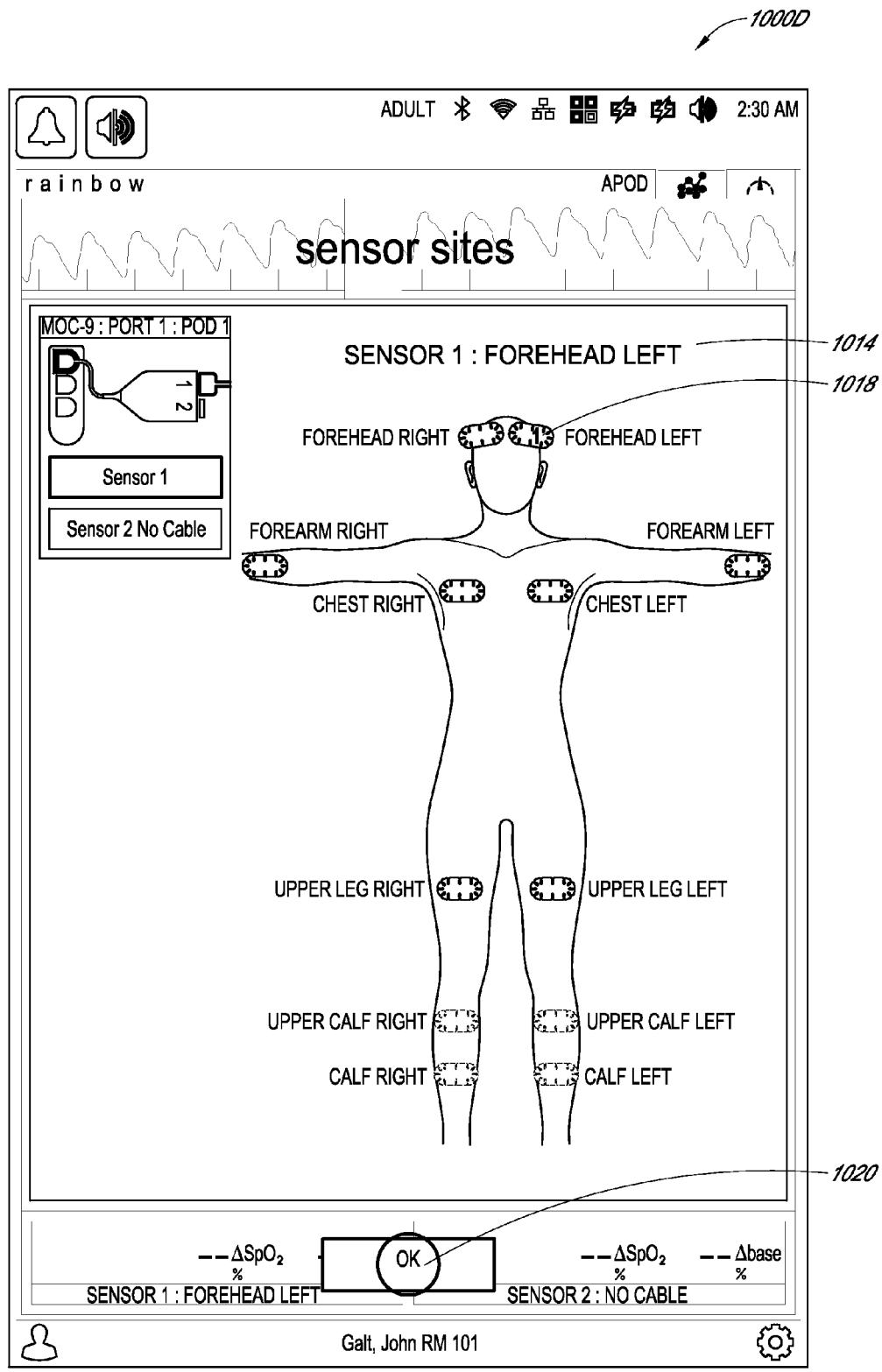

FIG. 10D illustrates a confirmation user interface display 1000D for selecting a first sensor site. The left forehead sensor site 1018 changes color, for example from white to blue, and the numeral "1" appears on the left forehead sensor site 1018, indicating that the sensor 1 site has been selected. Additionally the information line 1014 indicates that the sensor site has been selected by stating "SENSOR 1: FOREHEAD LEFT." The user is prompted to confirm the sensor site selection by touching an OK button 1020.

Figure 10E:
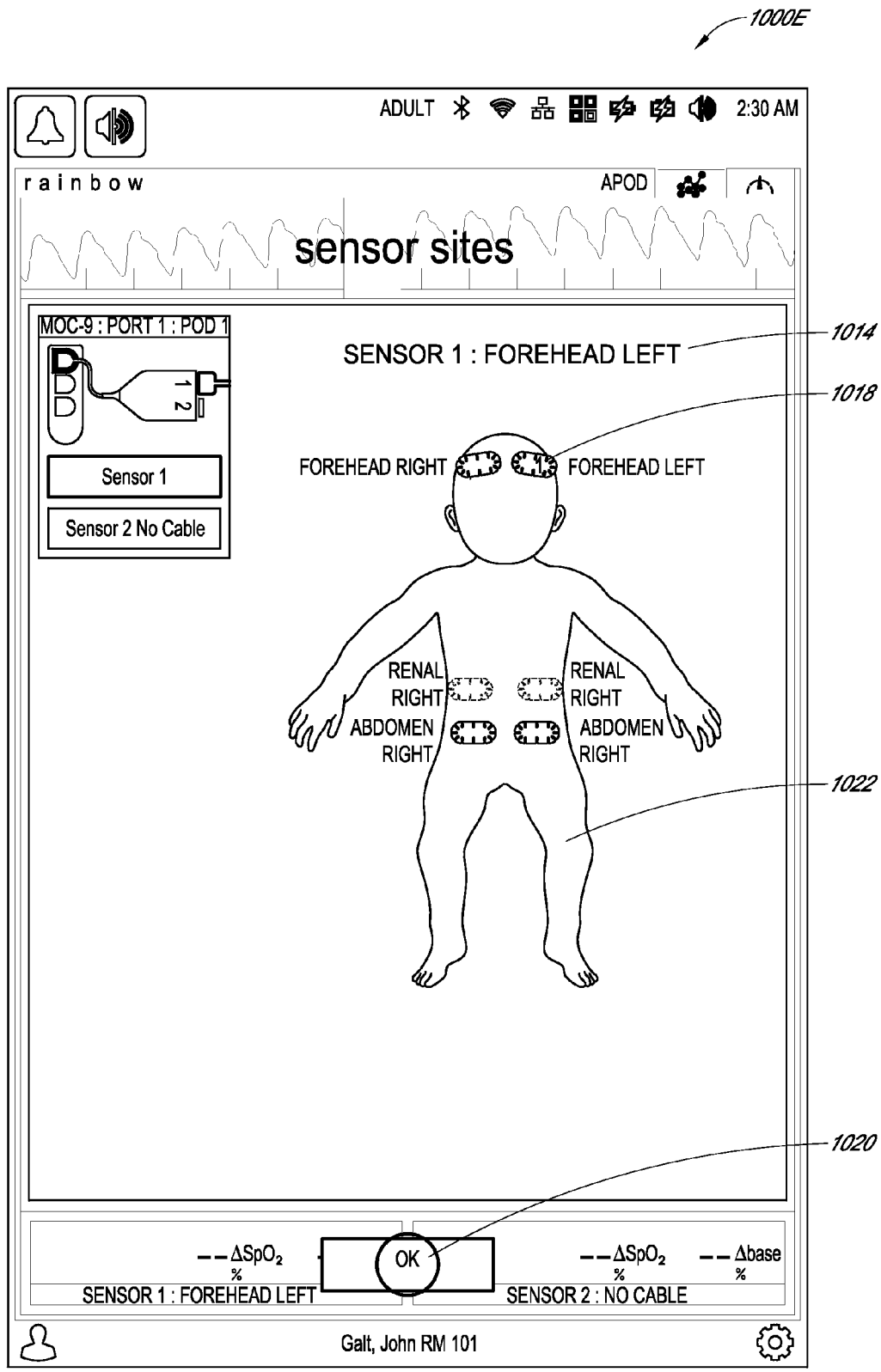

FIG. 10E illustrates an embodiment of a user interface in which the patient is a child 1000E. A child form 1022 is generated to display potential sites of the patient's body where a regional oximetry sensor can be placed, including right and left forehead, right and left renal and right and left abdomen. In this example, the left forehead sensor site 1018 changes color, for example from white to blue, and the numeral "1" appears on the left forehead sensor site 1018, indicating that the sensor 1 site has been selected. Additionally the information line 1014 indicates that the sensor site has been selected by stating "SENSOR 1: FOREHEAD LEFT." The user is prompted to confirm the sensor site selection by touching an "OK" button 1020.

Figure 10F:
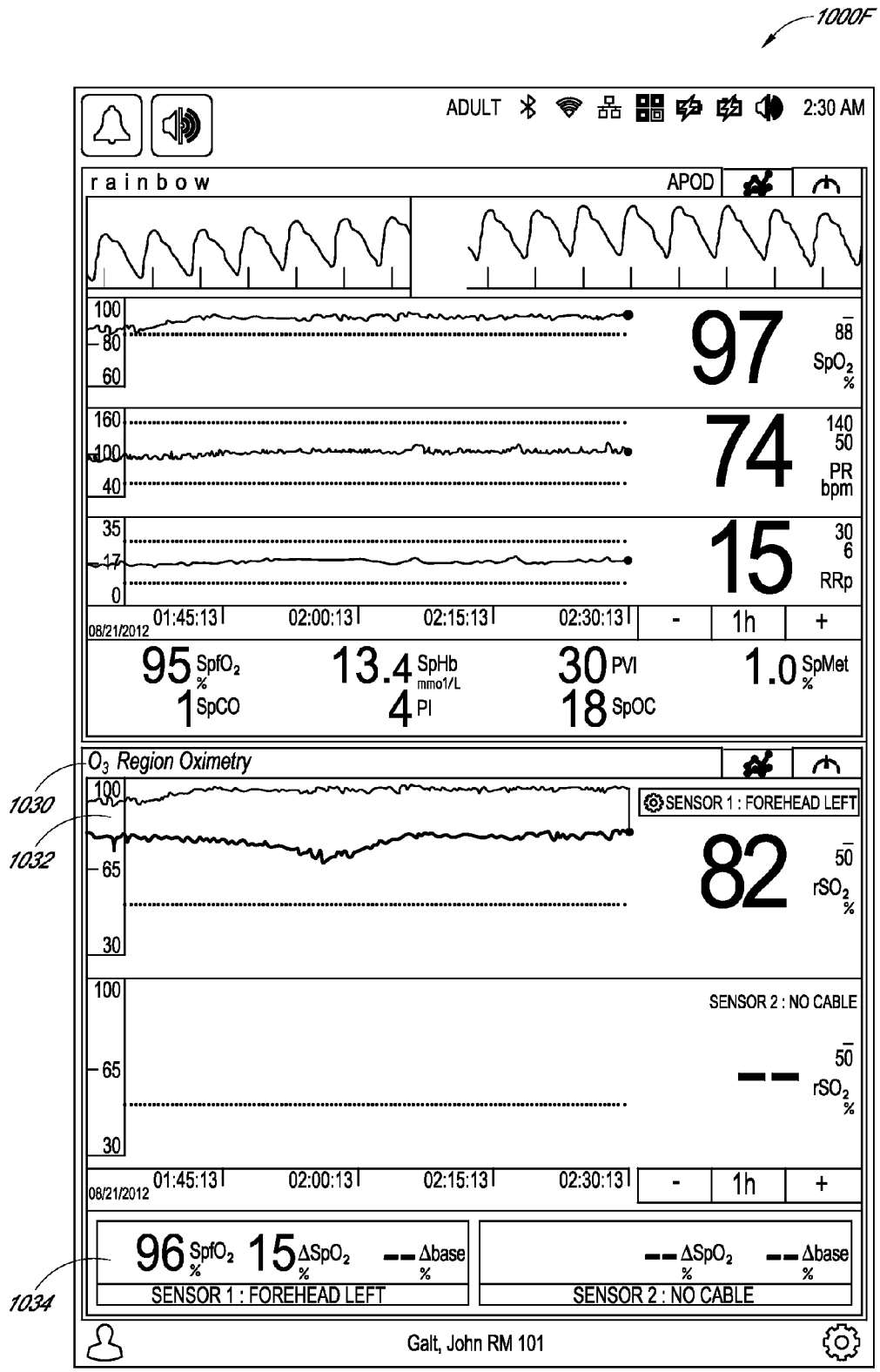

FIG. 10F illustrates an embodiment of a user interface display in which a sensor 1 is configured and monitoring the patient's regional oximetry of the left forehead 1000F. In this example, a two-sensor window 1030 is enabled for monitoring a forehead left site 1032,1034. Configuration of additional pods, selection of additional sensor sites, and modification of sensor sites can be performed in a similar manner to that described with respect to FIGS. 10A-F.

FIGS. 11A-11D illustrate embodiments of a user interface for setting a baseline for a regional oximetry sensor. The baseline is a reading of the patient's regional oximetry level before a patient is sedated. The baseline is compared with the patient's sedated regional oximetry measurements to assess whether the patient is being adequately oxygenated during, for example, a procedure.

Figure 11A:
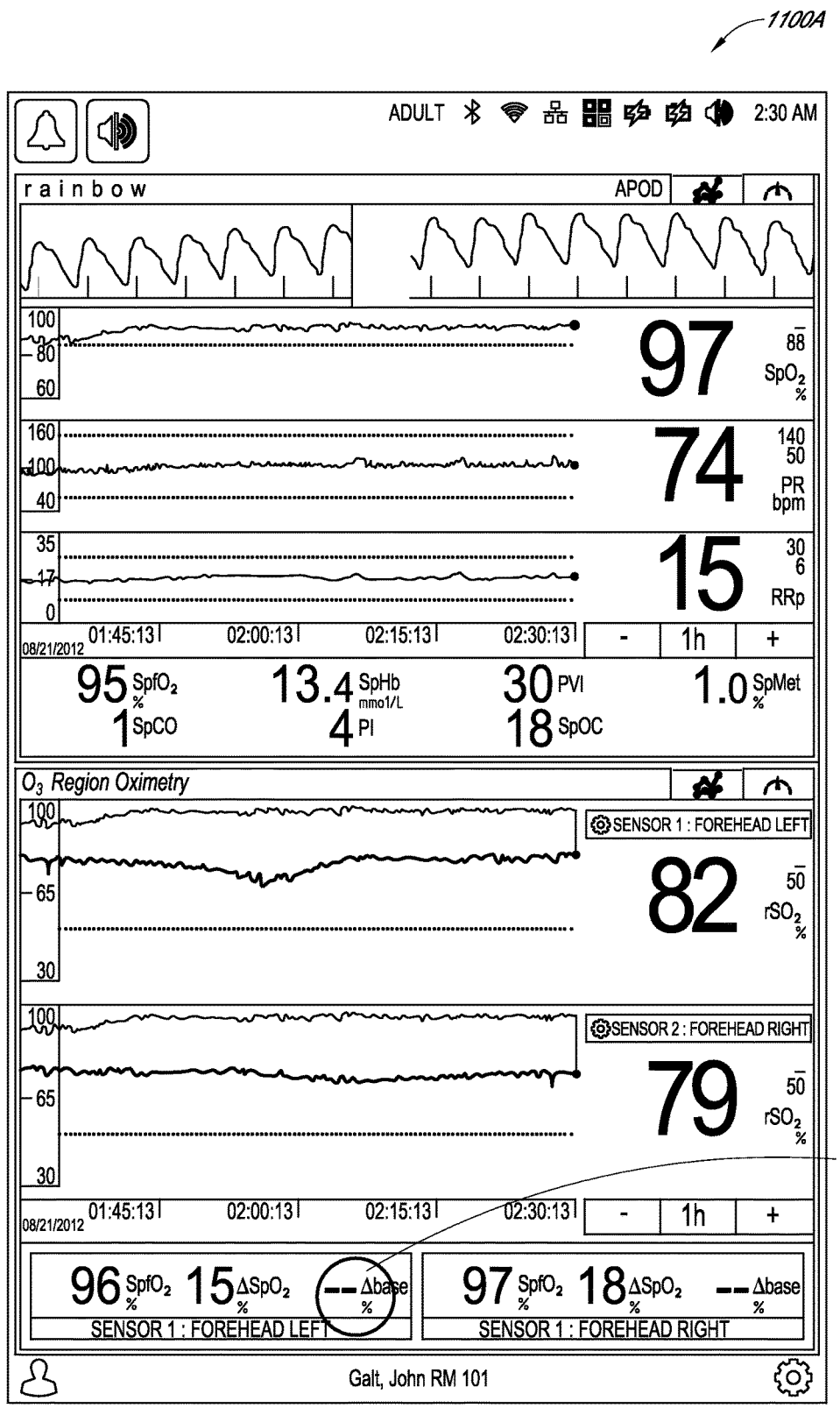
FIGS. 11A-11G illustrate embodiments of a user interface for setting a baseline for a regional oximetry sensor.
Figure 11B:
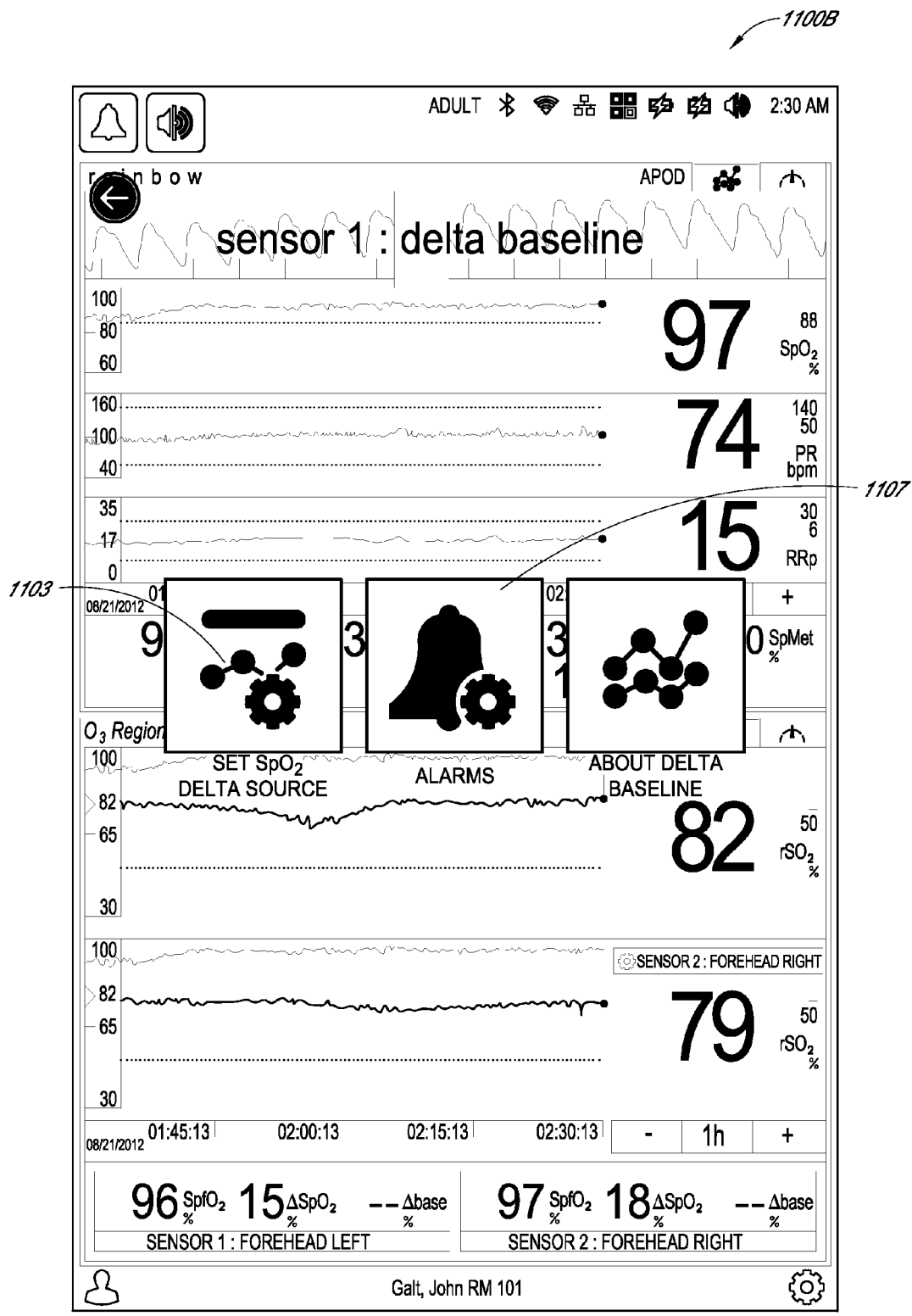
Figure 11C:
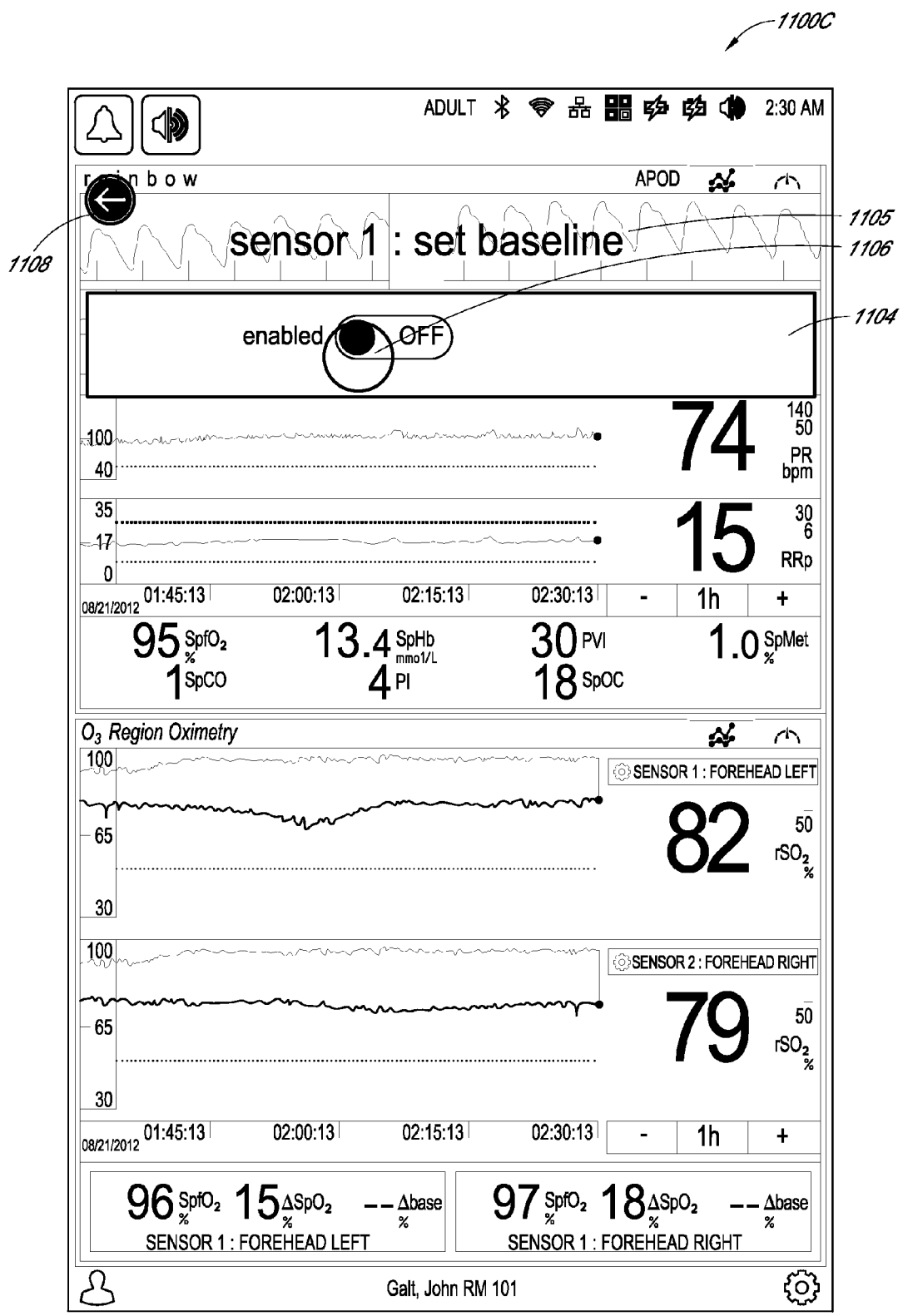
Figure 11D:
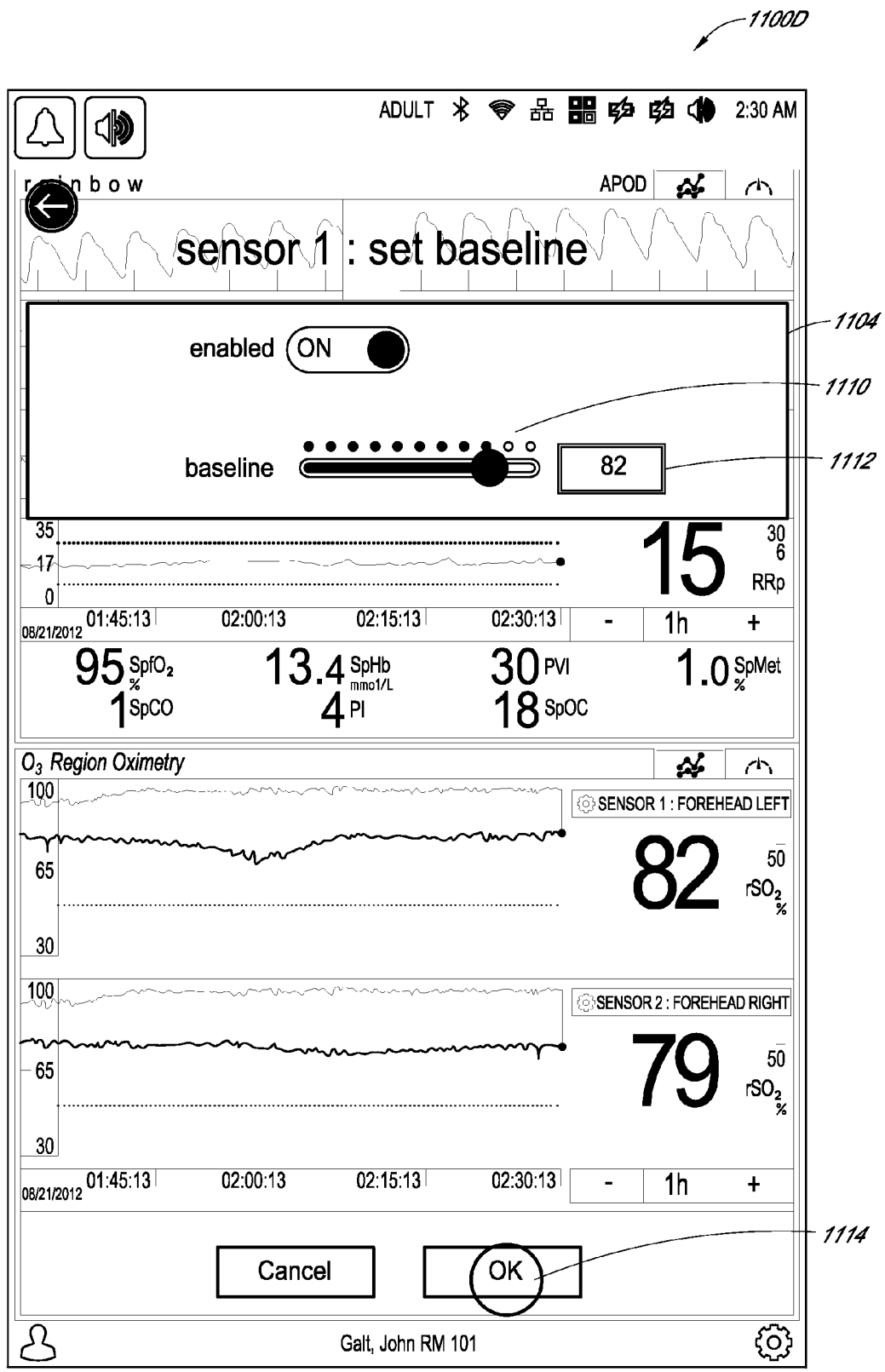
Figure 11E:
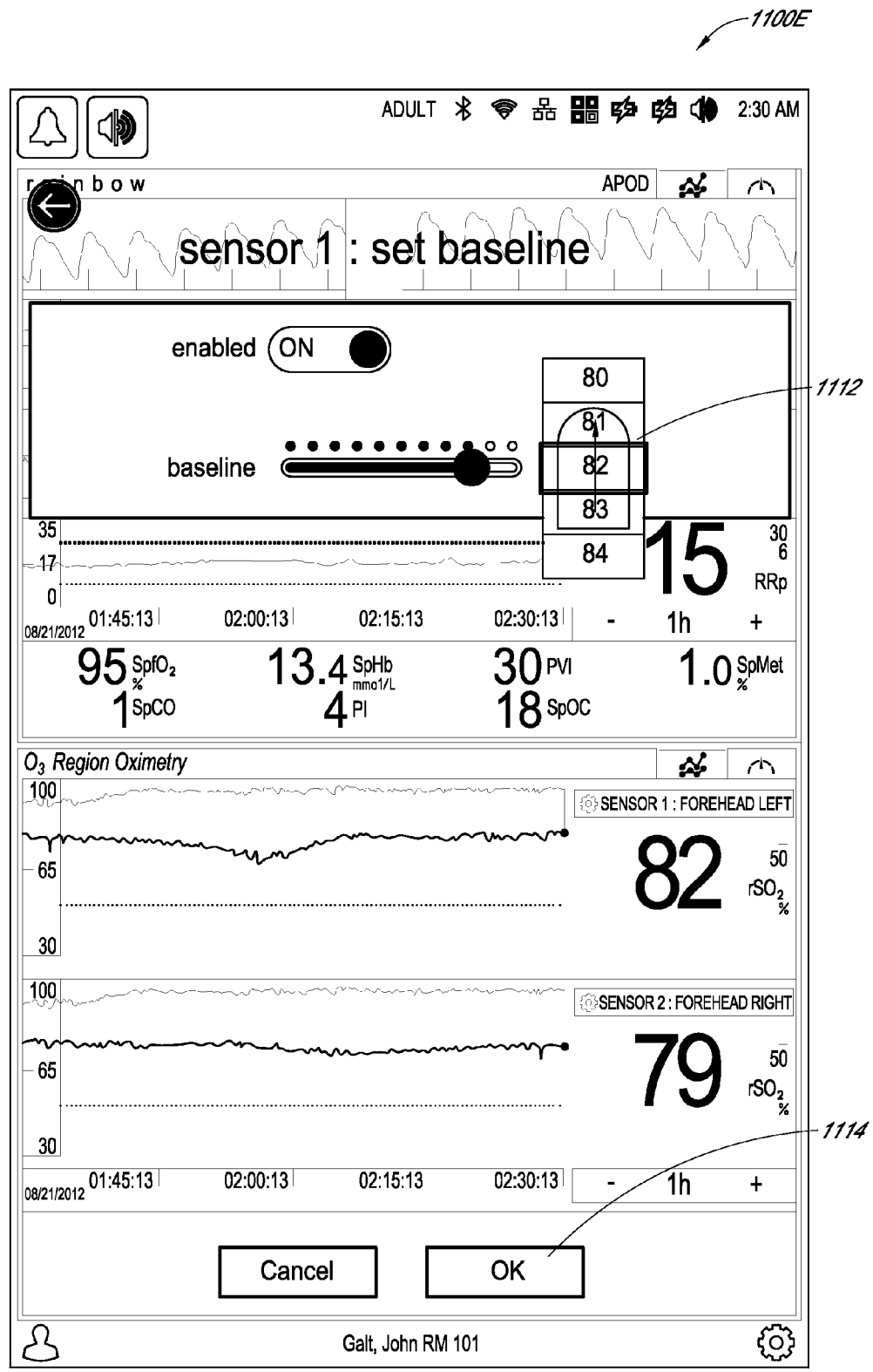
Figure 11F:
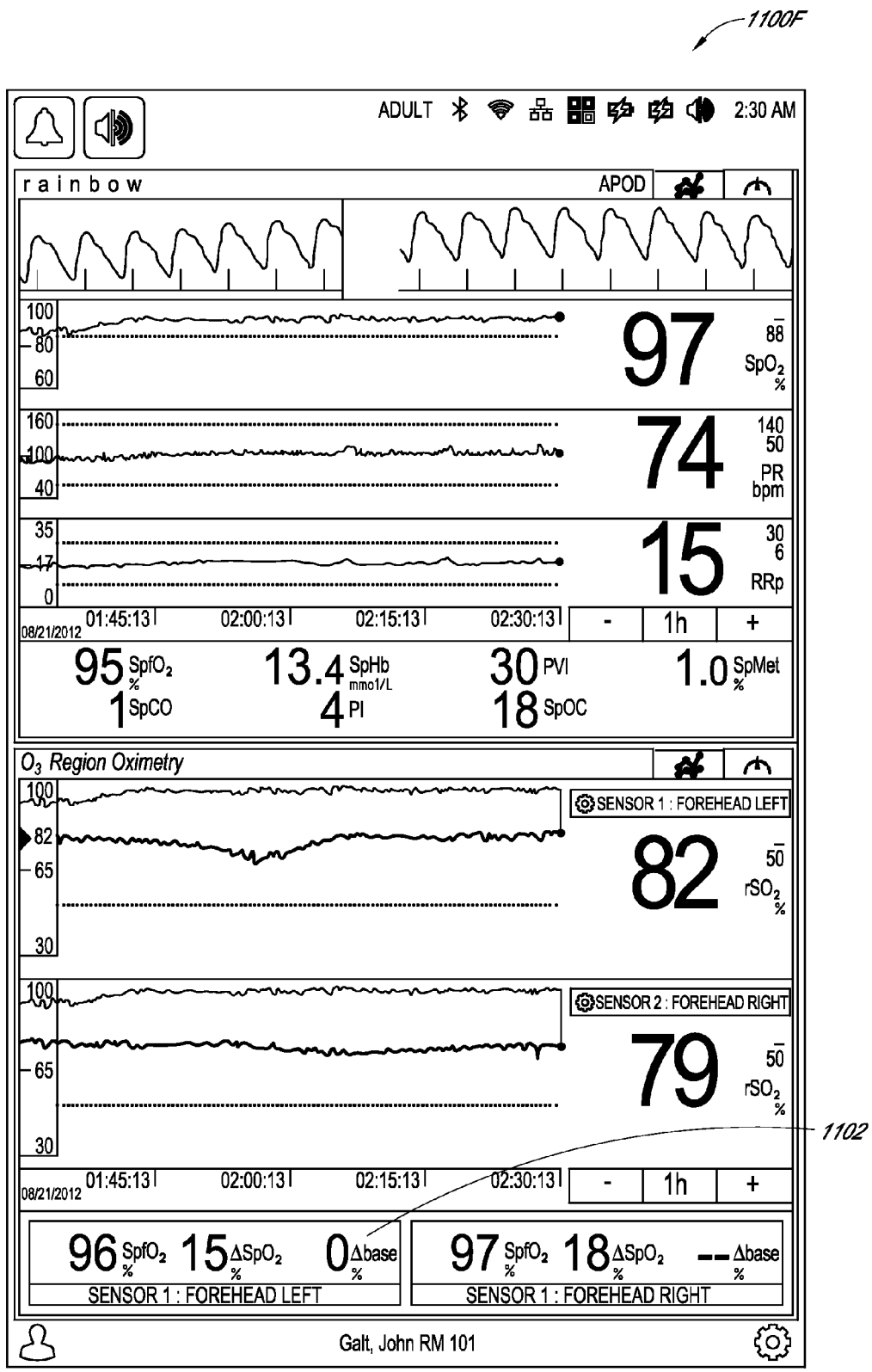

FIG. 11A illustrates an embodiment of a graphical display 1100A in which two regional oximetry sensors are positioned on the patient, where sensor 1 is positioned on the left forehead and sensor 2 is positioned on the right forehead. To initiate the process of setting a baseline for, say, sensor 1, the user selects a Δbase icon 1102 using a touch finger gesture 402. As illustrated in FIG. 11B, a sensor 1 delta baseline menu 1100B appears. By selecting the set baseline icon 1103, a set baseline display 1100C appears as illustrated in FIG. 11C. A baseline action screen 1104 appears with an information line 1105 instructing the user to set a baseline for sensor 1. The user enables the baseline feature for sensor 1 by sliding a toggle switch 1106 into the "on" position using, for example, a touch and move 406 finger control gesture. An arrow icon 1108 allows the user to navigate back to the previous screen if desired. Advantageously, while the user is engaged in configuring the hub 100 by engaging action screens, monitored data is displayed in the background with brightness reduced. FIG. 11D illustrates an updated set baseline display 1100D. The action screen 1104 expands to include a baseline setting slider 1110 and a numerical display 1112. As the user slides the baseline setting slider 1112 left or right, using for example the touch and move 406 finger control gesture, a corresponding numerical value is indicated on the numerical display 1112. FIG. 11E illustrates an embodiment 1100E in which the baseline is set by using a flick 408 finger control gesture on the numerical display 1112. In this example the user confirms the sensor site selection by touching an "OK" button 1114, and the action screen 1104 closes returning the user interface display 1100F to its previous level of brightness, as illustrated in FIG. 11F. The Δbase object 1102 now displays a numerical value, indicating that the baseline feature has been enabled and set. Setting baselines for additional sensor sites can be performed in a similar manner as to that described herein.

Figure 11G:
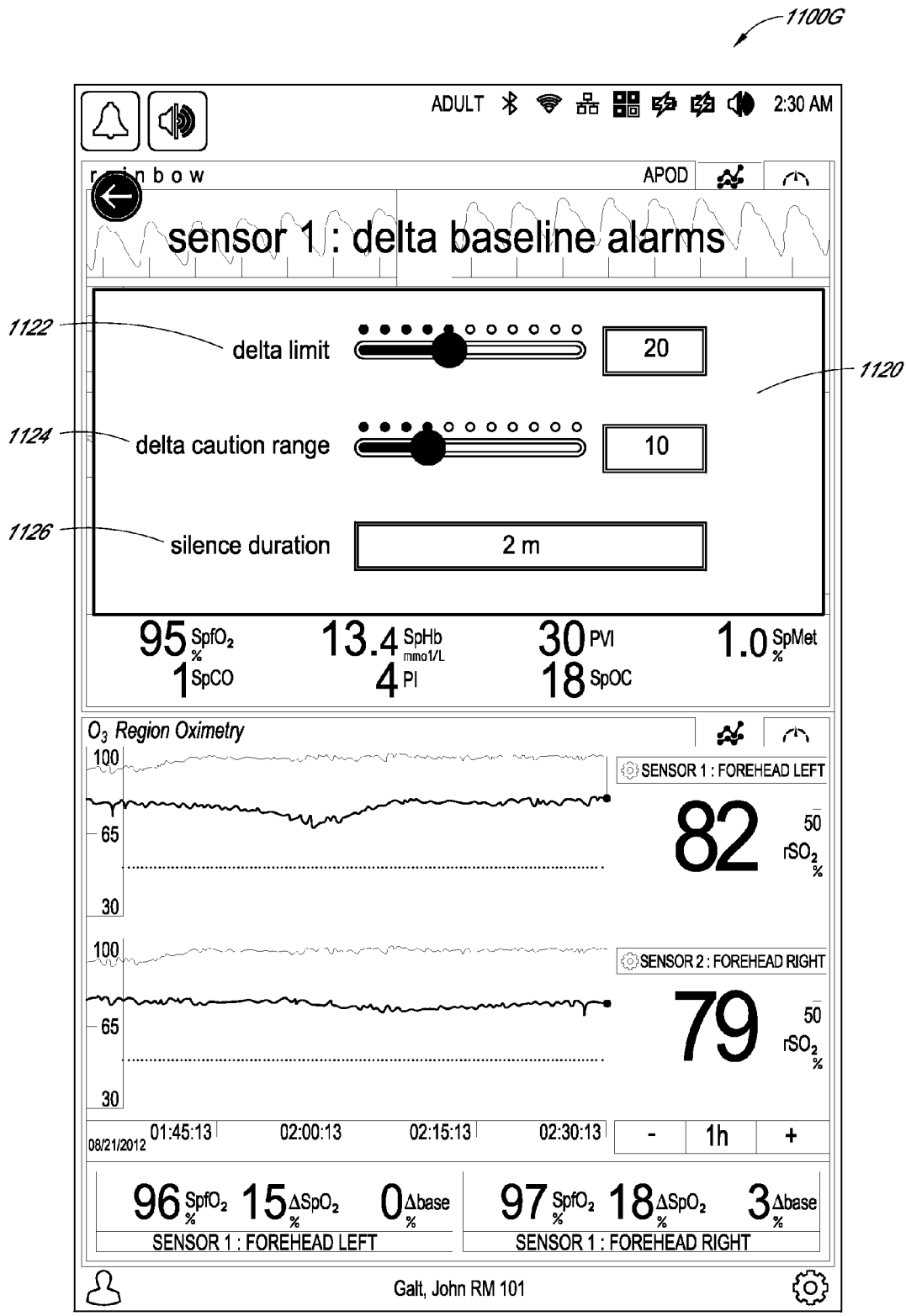

Referring back to FIG. 11B, by selecting the alarms icon 1107, the user navigates to a menu to set sensor 1 delta baseline alarms 1100G, illustrated in FIG. 11G. A delta baseline alarms action screen 1120 appears in which the user can set alarm conditions for the monitoring of sensor 1 delta baseline information. In an embodiment the alarm conditions include a delta limit 1122, a delta caution range 1124, and a silence duration 1126. Advantageously the alarm conditions can be used to graphically represent the status of the delta baseline metric on a trend view, as described below with respect to FIGS. 15A-B.

Figure 12A:
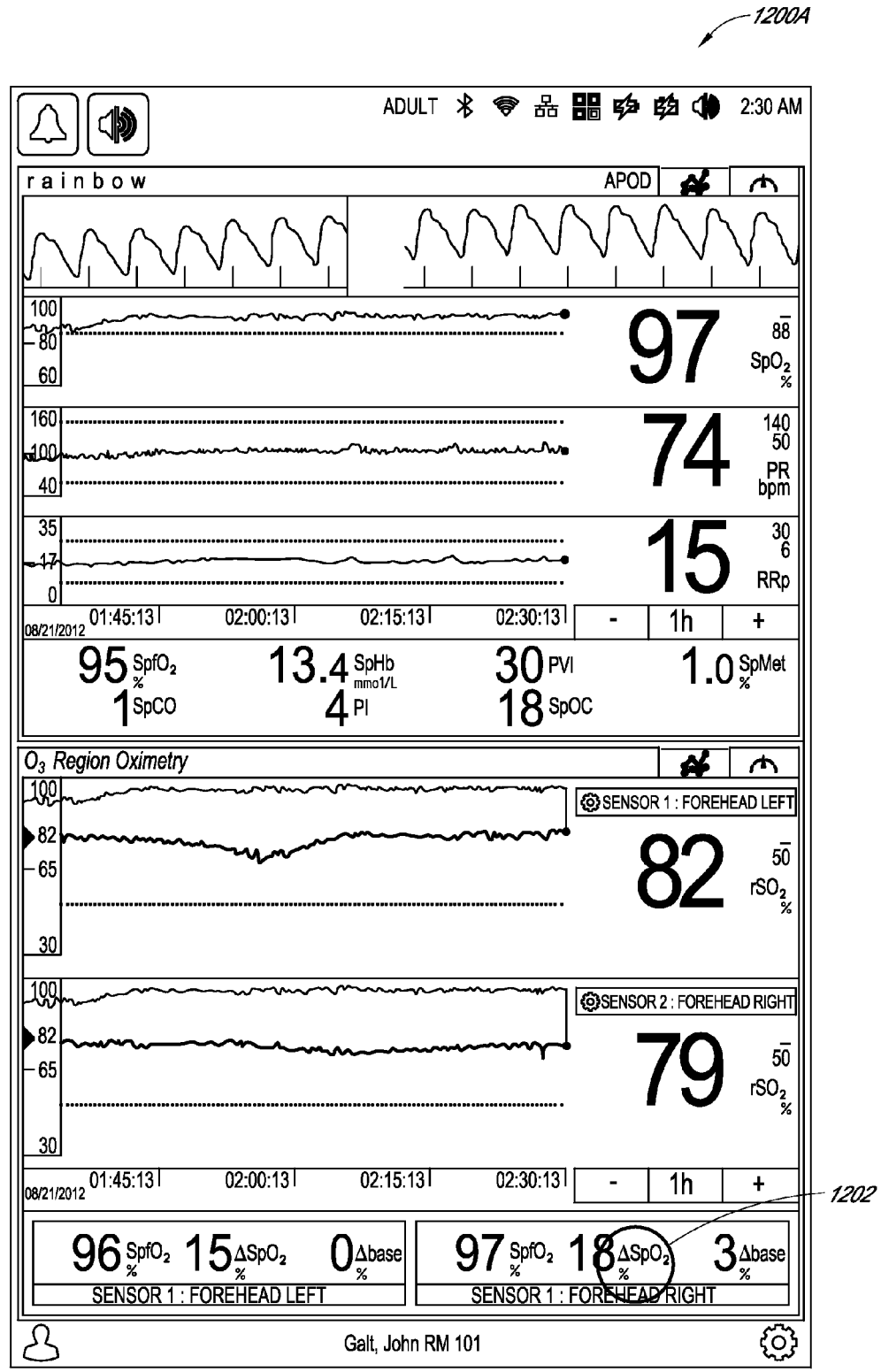
FIGS. 12A-12F illustrate embodiments of a user interface for setting a source for measuring arterial oxygen saturation.
Figure 12B:
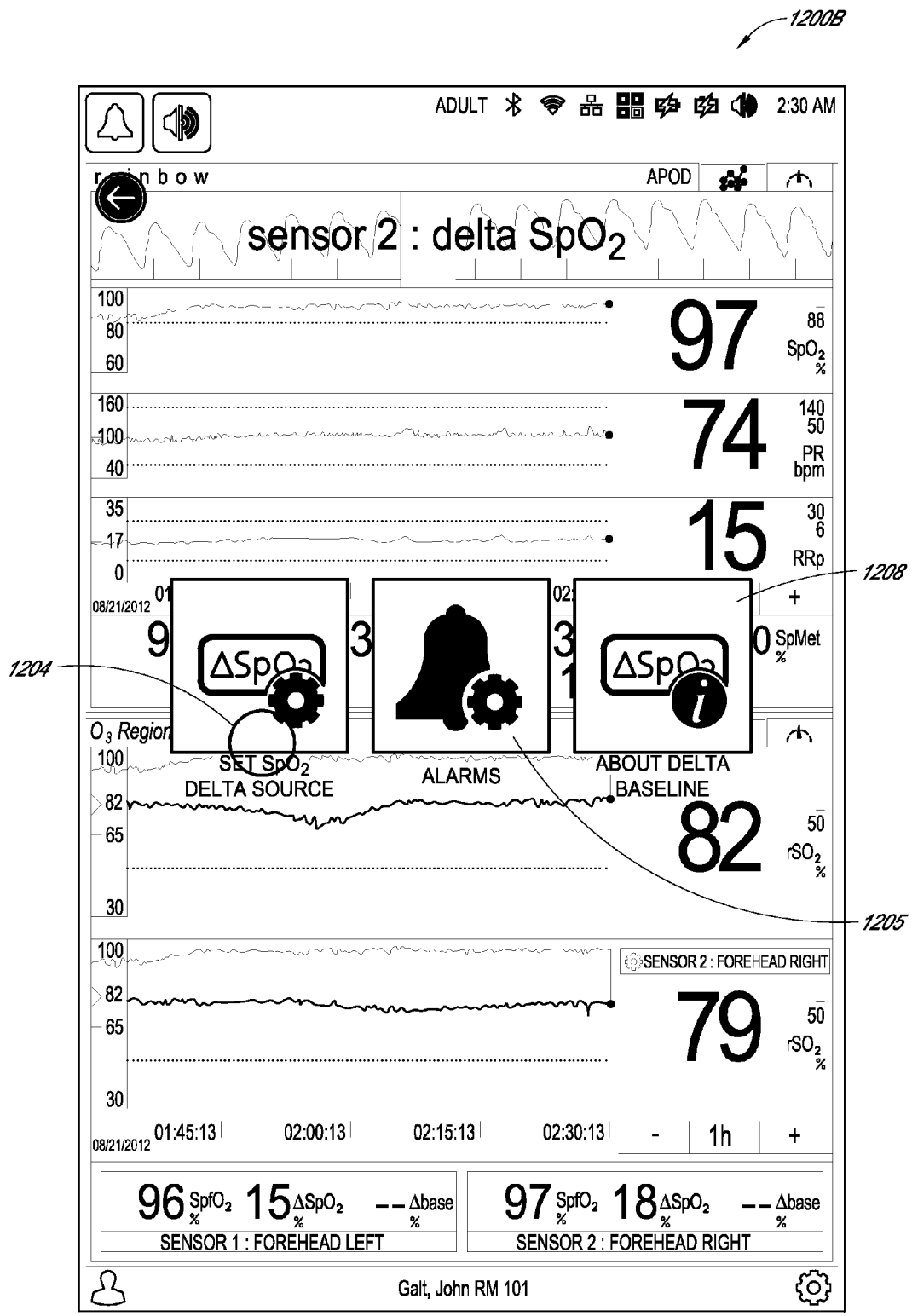
Figure 12C:
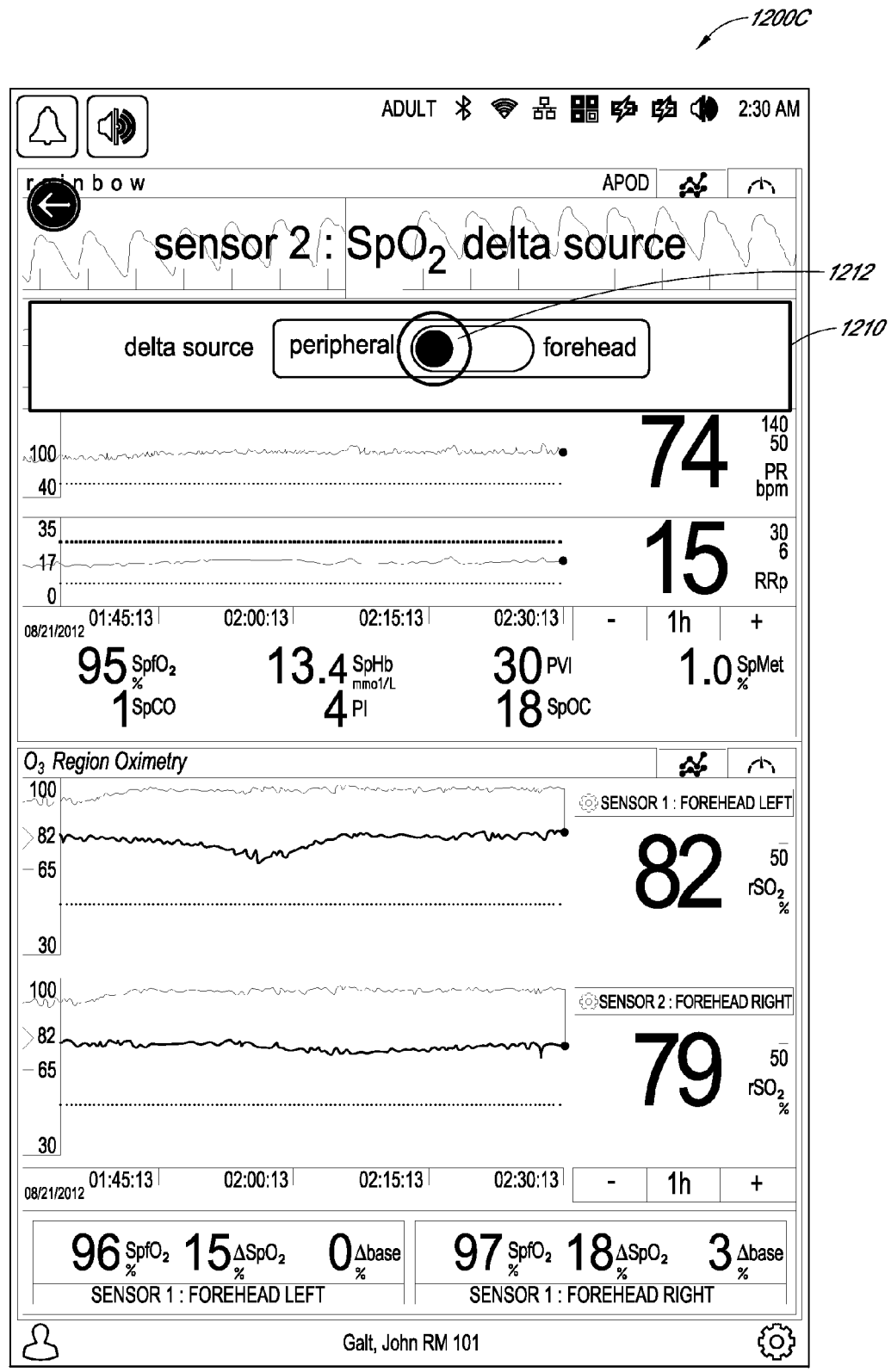
Figure 12D:
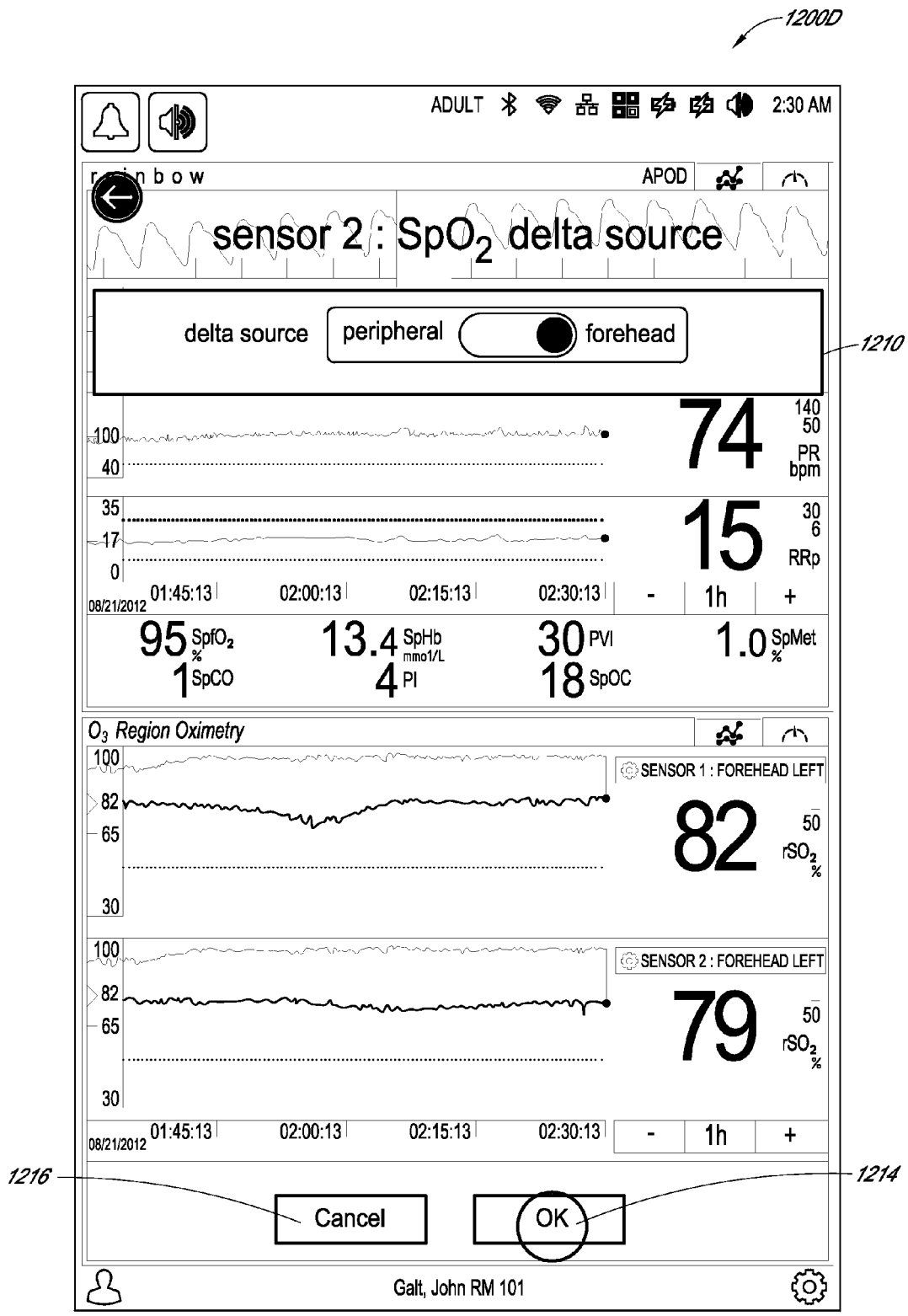
Figure 12E:
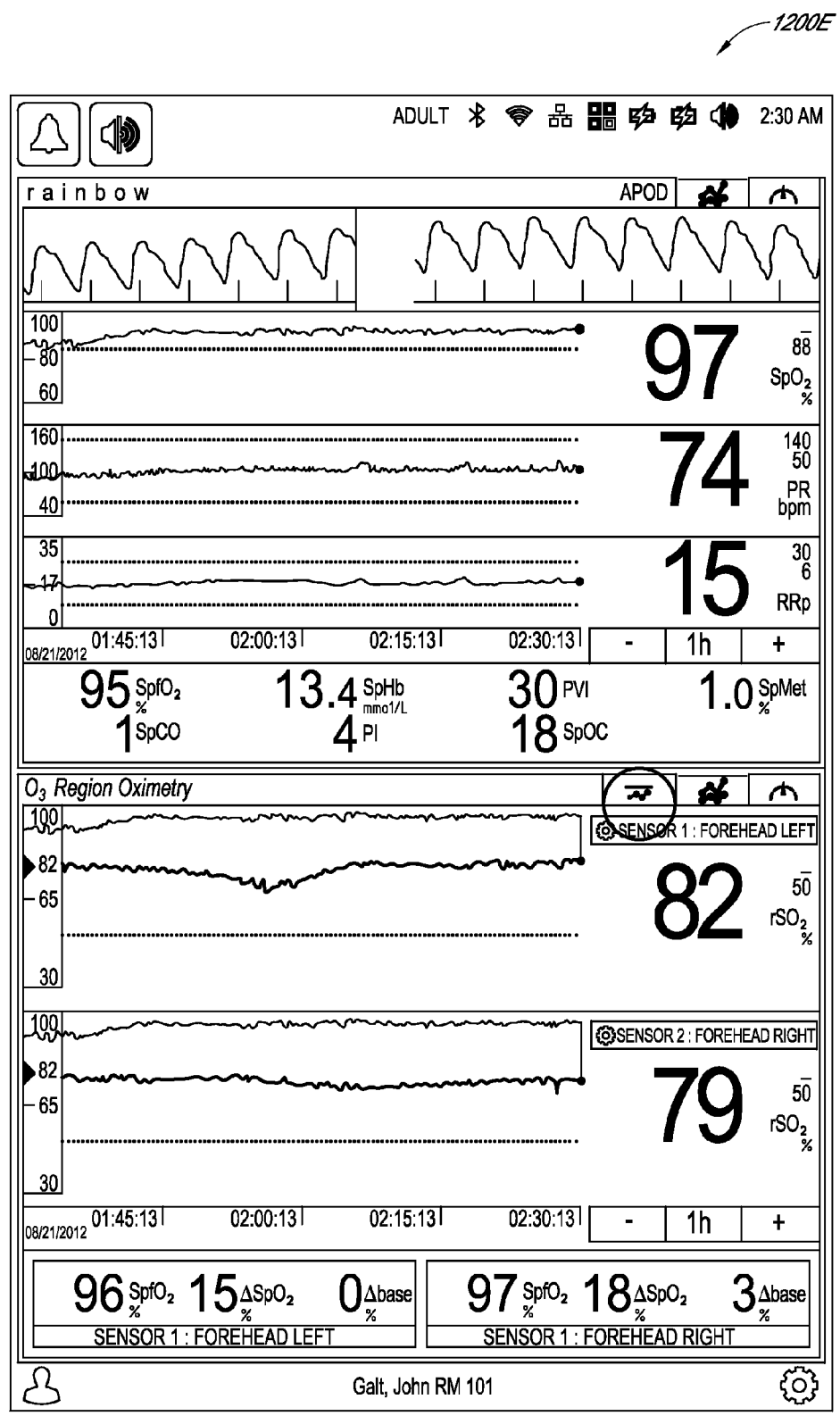

In an embodiment the hub 100 displays a differential analysis of a patient's regional-to-central oxygen saturation, also referred to as $\Delta SpO_2$, where measurement of the patient's arterial oxygen saturation is compared with one or more measurements of regional oxygen saturation. The source of measurements of the patient's arterial oxygen saturation used to determine the patient's regional-to-central oxygen saturation can be provided by the regional oximetry sensor or by a peripheral arterial oxygen sensor. FIGS. 12A-12E illustrate embodiments of a user interface for setting a source for measuring arterial oxygen saturation for determining a patient's regional-to-central oxygen saturation. FIG. 12A illustrates an embodiment of a user interface 1200A in which two regional oximetry sensors are positioned on the patient, where sensor 1 is positioned on the left forehead and sensor 2 is positioned on the right forehead. To initiate the process of setting a delta $SpO_2$ source for, say, sensor 2, the user selects a $\Delta SpO_2$ icon 1202 using a touch finger gesture 402. As illustrated in FIG. 12B, a delta $SpO_2$ screen 1200B appears with three delta $SpO_2$ menu icons on the display including a "set $SpO_2$ delta source" icon 1204, an "alarms" icon 1206, and an "about delta baseline" icon 1208. When the user selects the "set $SpO_2$ delta source" icon 1204, an SpO2 delta source display 1200C appears. A delta source action screen 1210 appears, as illustrated in FIG. 12C. The information line instructs the user to select an SpO2 delta source for sensor 2. The user selects the SpO2 delta source for sensor 2, in this case, by sliding a toggle switch icon 1212 either to the regional oximetry sensor location—which in this case is identified as forehead—or to a peripheral setting, using a touch and move 406 finger control gesture. As illustrated in FIG. 12D, once the SpO2 delta source is selected (to forehead in this illustration) the user is prompted to confirm the delta source selection by touching an "OK" button 1214. Alternatively, the user can cancel the delta source selection by touching a "cancel" button 1216. The action screen 1210 then closes returning the main display 1200E to its previous level of brightness, as illustrated in FIG. 12E, indicating that in this embodiment, the sensor 2 $SpO_2$ delta source is set.

Figure 12F:
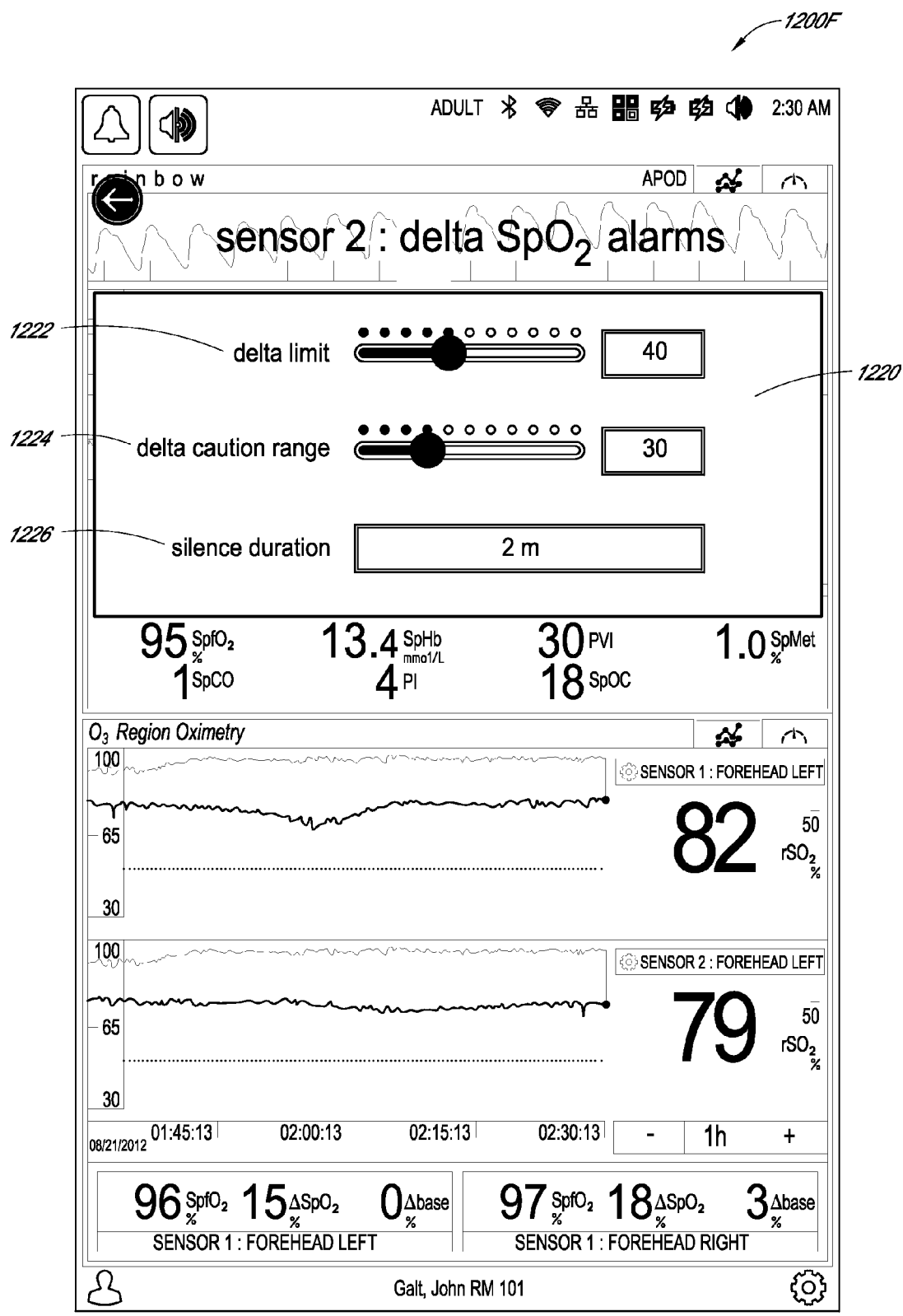

Referring back to FIG. 12B, by selecting the alarms icon 1205, the user navigates to a menu to set sensor 2 delta $SpO_2$ alarms 1200F, illustrated in FIG. 12F. A delta baseline alarms action screen 1220 appears in which the user can set alarm conditions for the monitoring of sensor 2 delta baseline information, including a delta limit 1222, a delta caution range 1224, and a silence duration 1226.

Figure 13A:
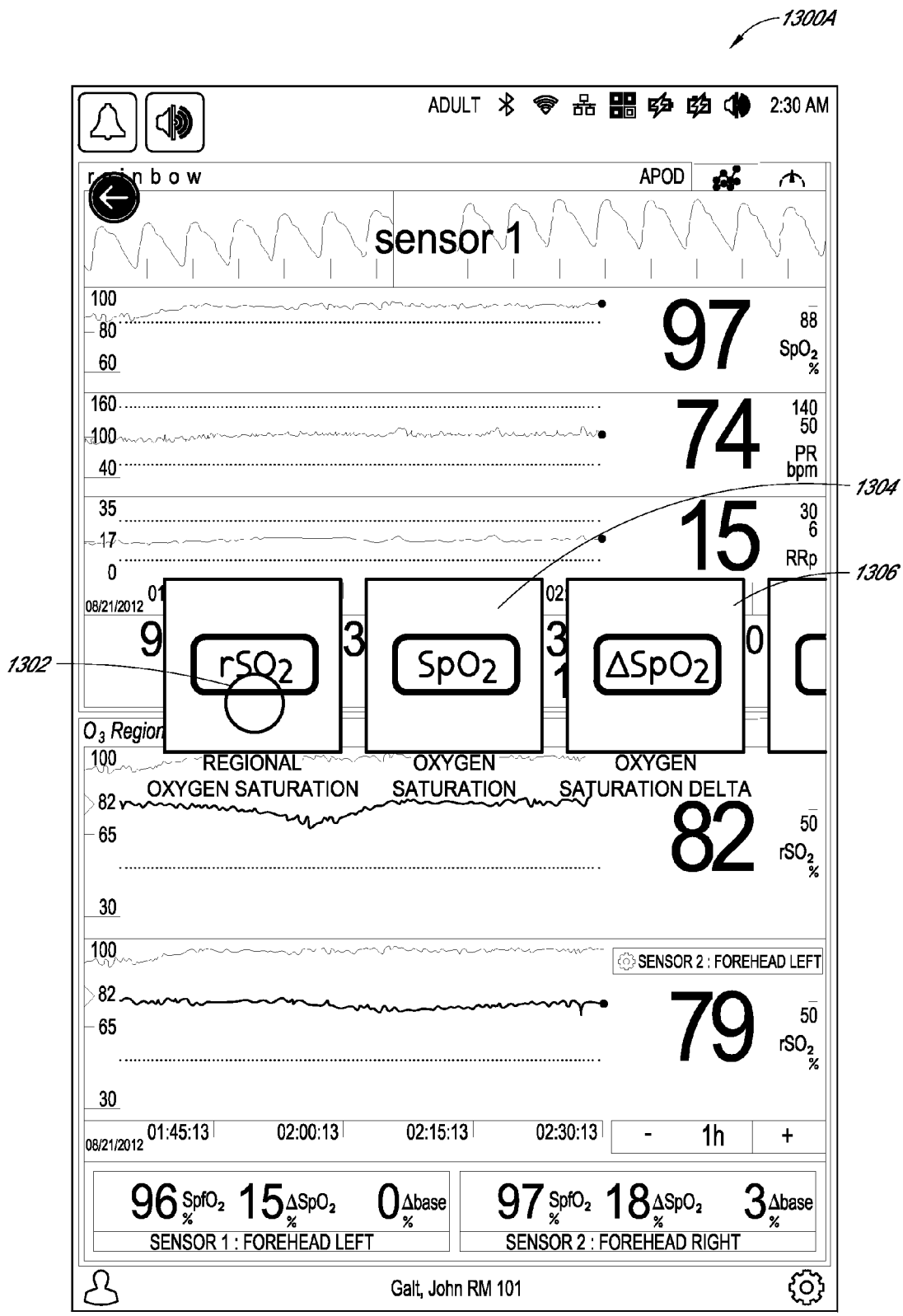
FIGS. 13A-13E illustrate embodiments of a user interface for setting parameters of a sensor used in a regional oximetry system.
Figure 13B:
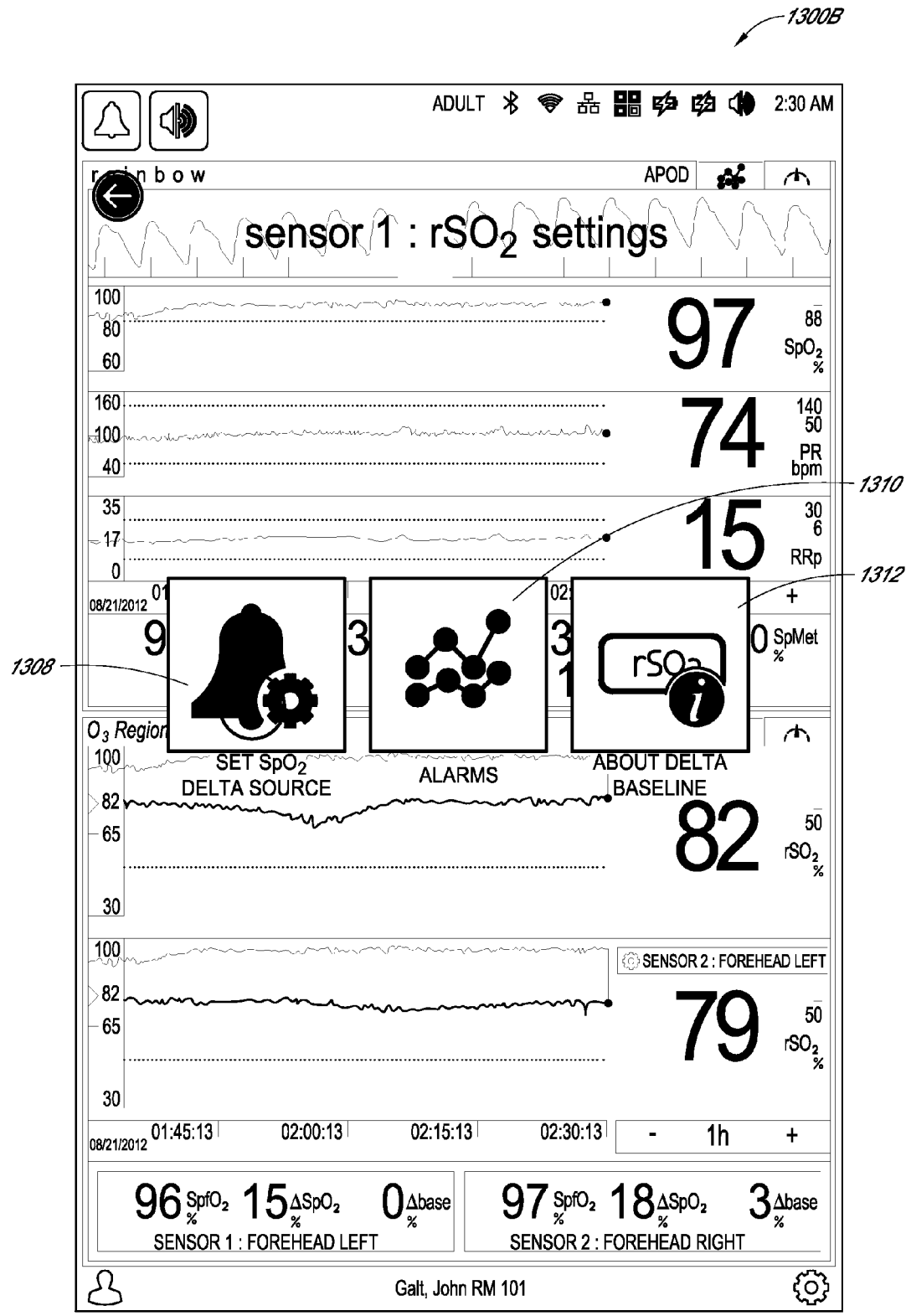
Figure 13C:
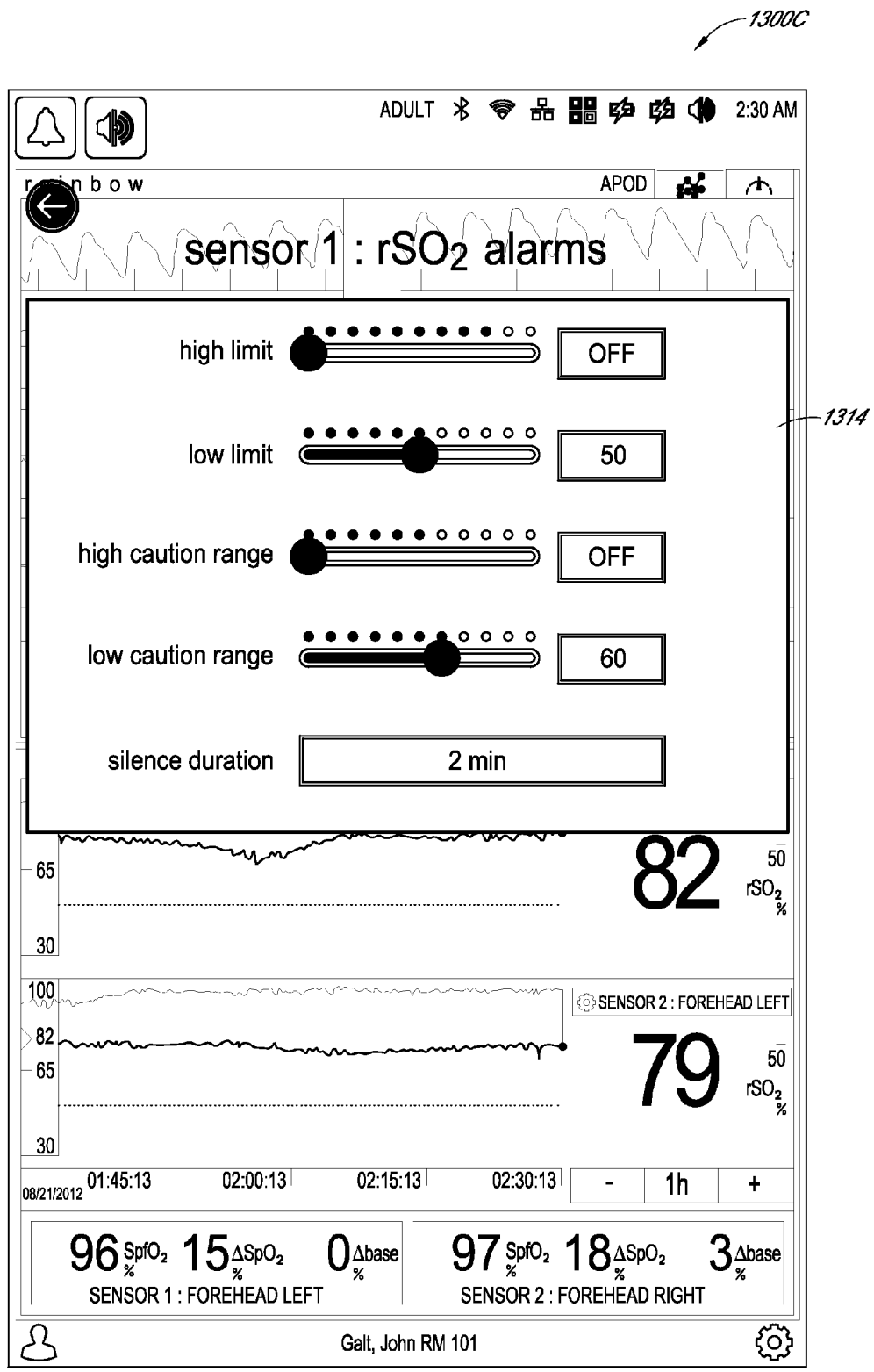

FIGS. 13A-13E illustrate embodiments of a user interface for setting parameters of a sensor used in a regional oximetry system to operate with the hub 100. The user navigates from the main menu and the regional oximetry menu (described above with respect to FIGS. 10A-B) to arrive at, say, a sensor 1 menu 1300A, as illustrated in FIG. 13A. By selecting a regional oxygen saturation icon 1302, the user navigates to a menu for sensor 1 regional oxygen saturation ($rSO_2$) settings 1300B as illustrated in FIG. 13B. Similarly, by selecting an alarms icon 1308, the user navigates to a screen for setting sensor 1 $rSo_2$ alarms 1300C which displays an action screen 1314 for setting sensor 1 regional oxygen saturation ($rSO_2$) alarms, as illustrated in FIG. 13C. In an embodiment the alarms include high limit, low limit, high caution range, low caution range, and silence duration. The action screen 1314 features buttons to turn on or off various alarms and sliders by which the user can set parameters, such as limits, ranges and durations, to establish alarm triggering conditions for a given sensor positioned on a patient.

Figure 13D:
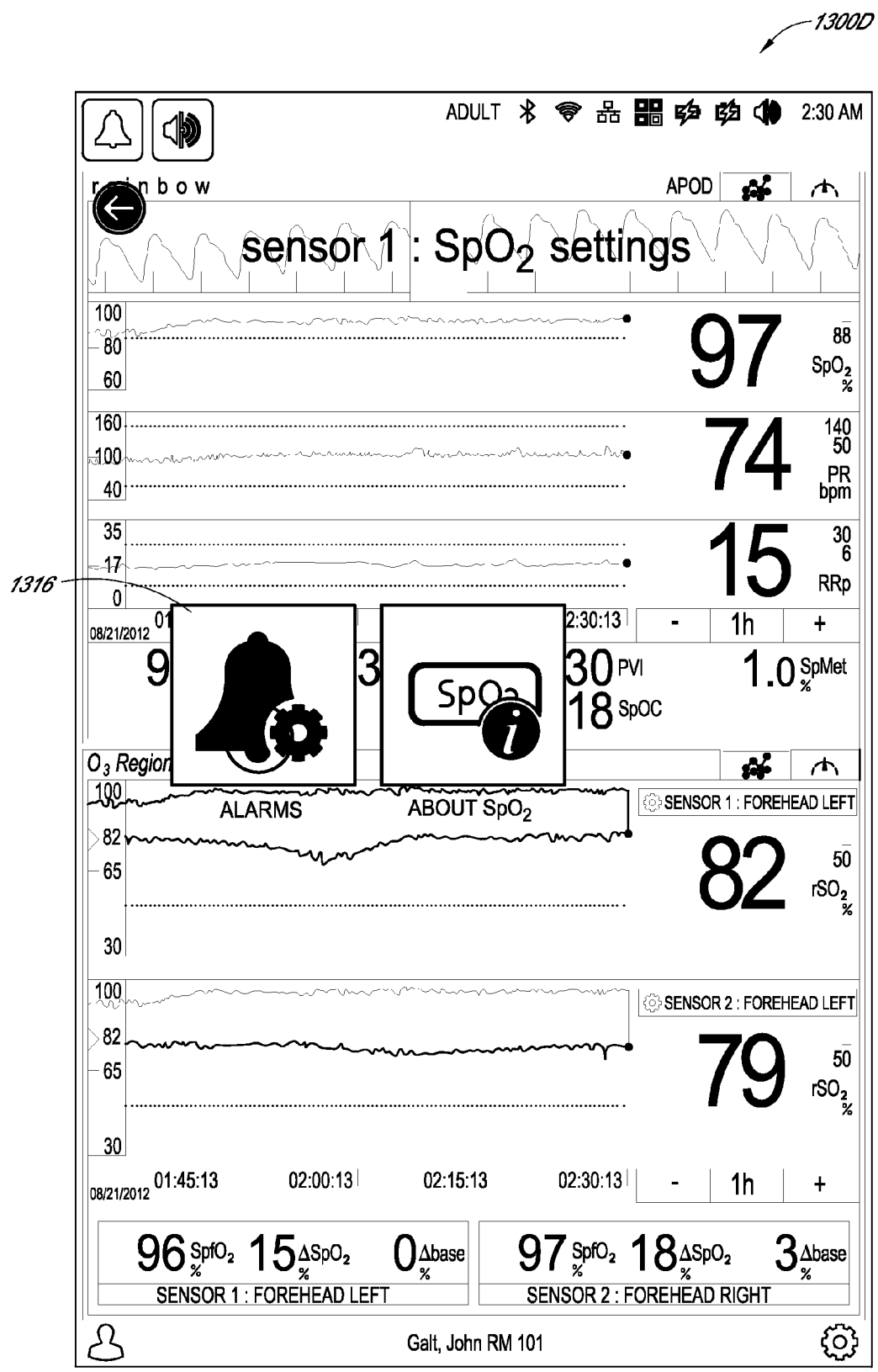
Figure 13E:
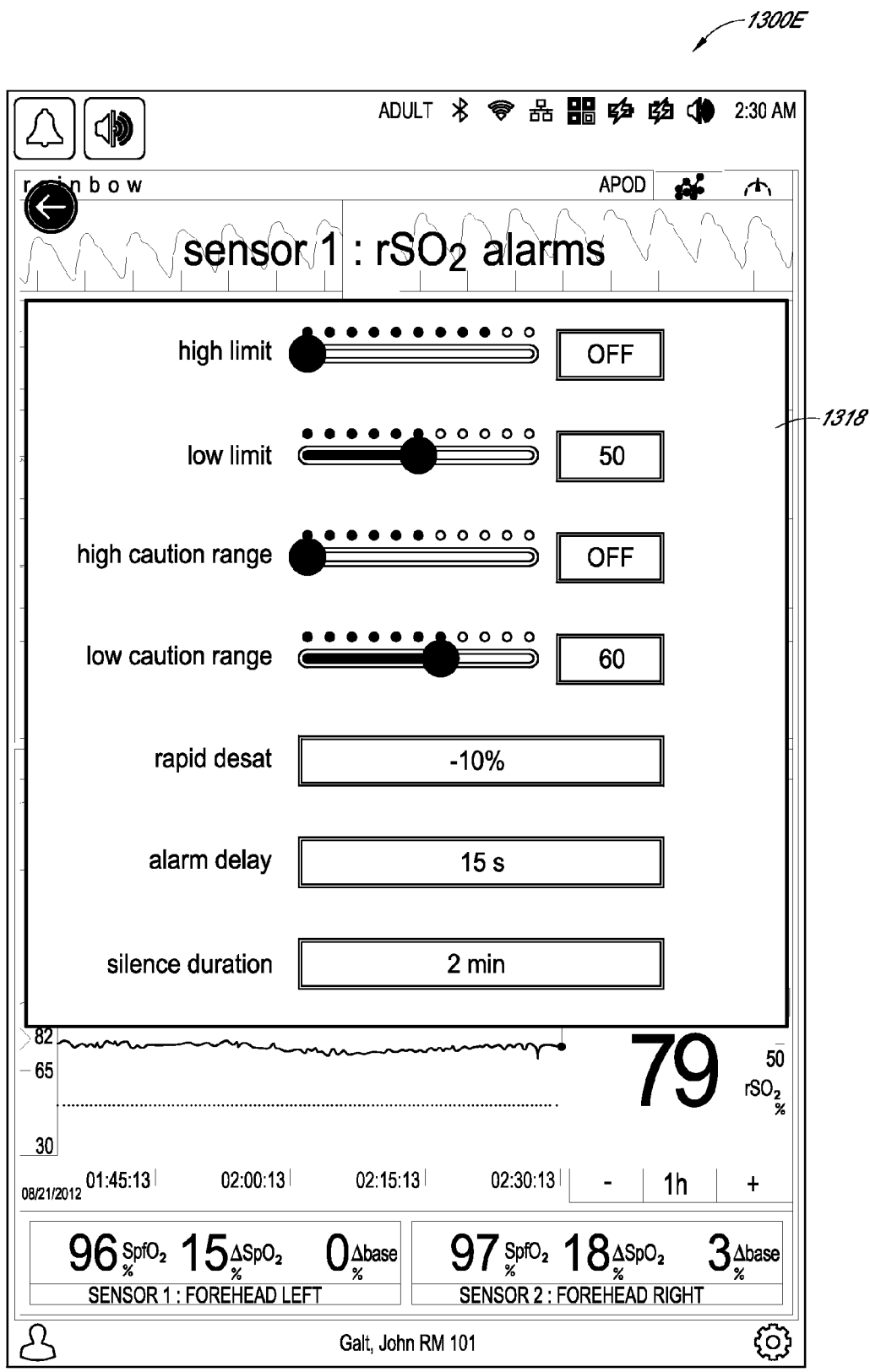

Referring back to the sensor menu of FIG. 13A, the user can select the oxygen saturation icon 1304 to navigate to, for example, the sensor 1 oxygen saturation ($SpO_2$) settings menu 1300D, illustrated in FIG. 13D. By selecting an alarms icon 1316, the user navigates to a sensor 1 SpO2 alarms menu 1300E displaying an action screen 1318 for setting sensor 1 oxygen saturation ($SpO_2$) alarms, as illustrated in FIG. 13E. In an embodiment the alarms include high limit, low limit, high caution range, low caution range, rapid desaturation, alarm delay and silence duration. The action screen 1318 features buttons to turn on or off various alarms, sliders by which the user can set parameters, such as limits, ranges and durations, to establish alarm triggering conditions for a given patient. Advantageously the alarm conditions can be used to graphically represent the status of the delta baseline metric on a trend view, as described below with respect to FIGS. 15A-B.

Figure 14:
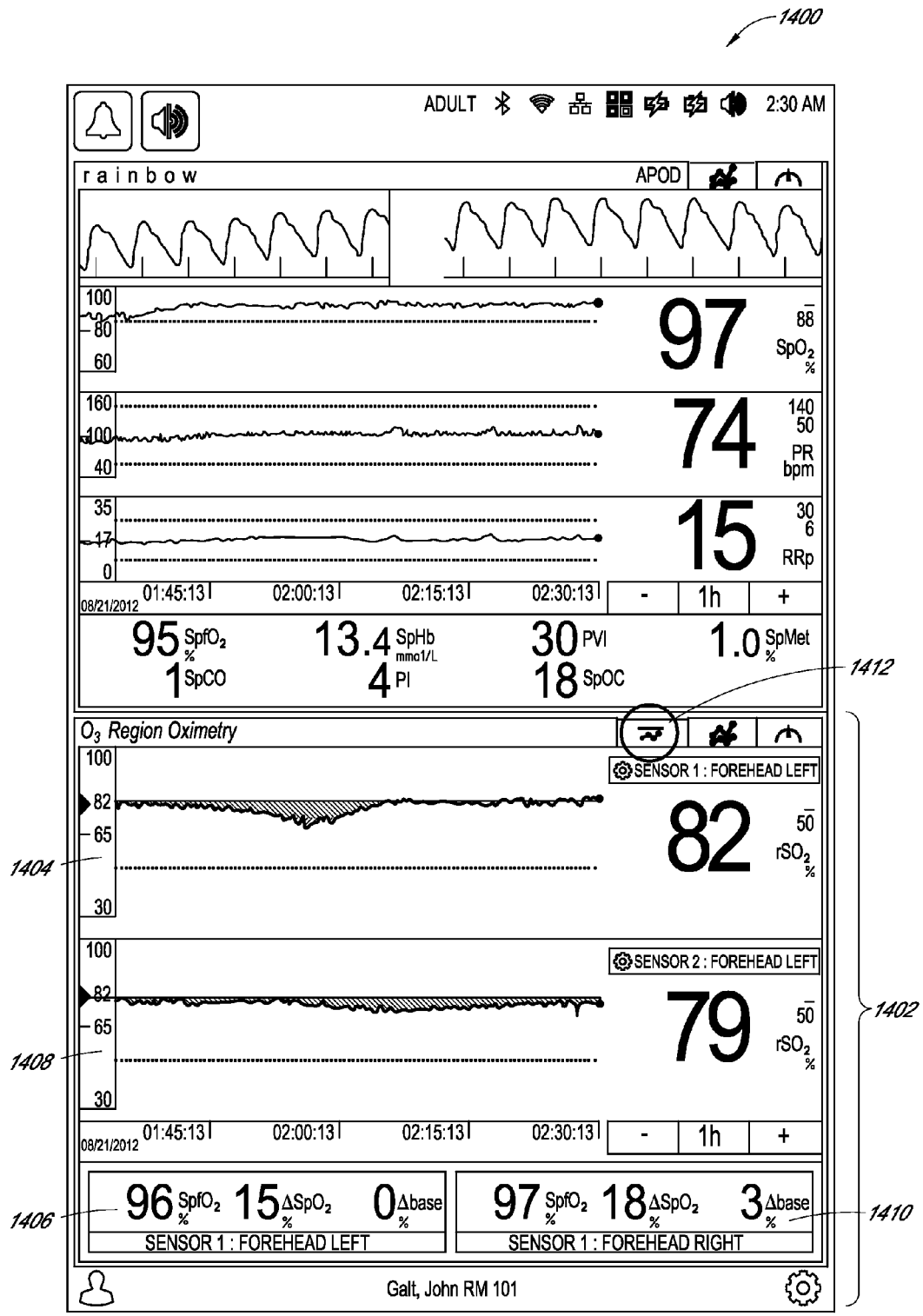
FIG. 14 illustrates an embodiment of a display of regional oximetry baseline delta measurements.

FIG. 14 illustrates an embodiment of a monitor display 1400 in which regional oximetry baseline delta measurements are presented. In this embodiment a two-sensor display 1402 is configured to present monitored patient data from the patient's left forehead 1404, 1406 and from the patient's right forehead 1408, 1410. A baseline view icon 1412 is selected which results in formatting the patient's measured data to be presented graphically, with a baseline that has been set by the user, at the trend displays 1404,1408. In the present example illustrated in FIG. 14 the baseline is set to 82 for both sensor 1 (positioned on the patient's left forehead) and sensor 2 (positioned on the patient's right forehead). Accordingly the user readily sees differences between the measured regional oximetry and a baseline level. Additionally, the present difference between the measured regional oximetry and the baseline is displayed numerically at well displays 1406,1410 next to the Δbase label.

Figure 15A:
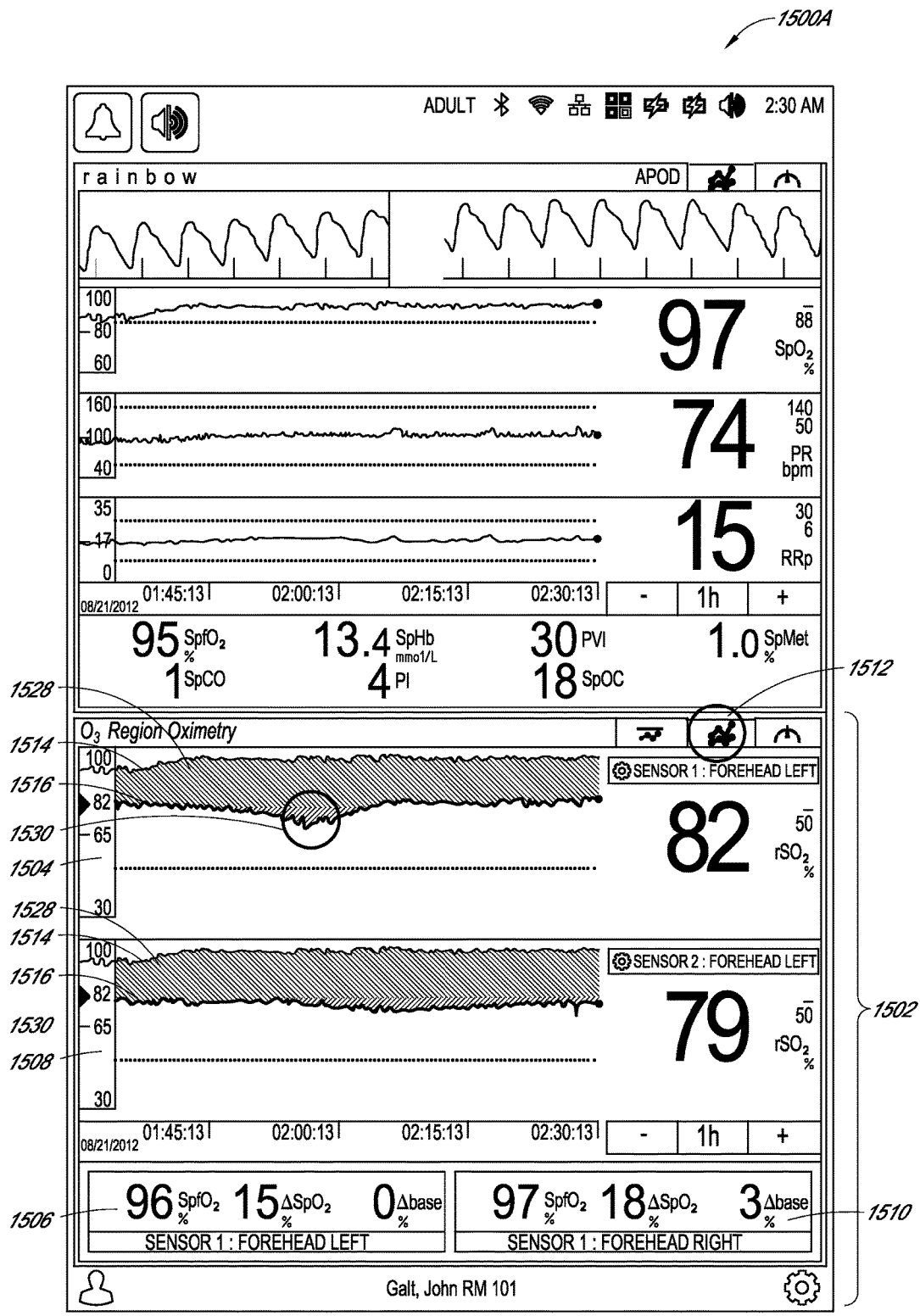
FIGS. 15A-15B illustrate embodiments of a display of regional-to-central oxygenation saturation measurements.

FIG. 15A illustrates an embodiment of a monitor display 1500A in which, among other things, the patient's regional-to-central oxygenation saturation measurements, or $SpO_2$ delta, are presented. In this embodiment a two-sensor window display 1502 is configured to present monitored patient data from the patient's left forehead 1504, 1506 and from the patient's right forehead 1508, 1510. A trend view icon 1512 is selected which, in this example, results in formatting the patient's measured data to be presented graphically with two trend lines: a first line representing measured arterial oxygen saturation 1514 and a second line representing regional oxygen saturation 1516 thereby visually reflecting the difference between the two measurements. In an embodiment the first line 1514 is displayed in a first color, for example, white, and the second line 1516 is displayed in a second color, for example, blue. Accordingly the user readily sees differences between the measured arterial oxygen saturation and the measured regional oxygen saturation and is able to distinguish one measurement form the other. Additionally, the present difference between the measured arterial oxygen saturation and measured regional oxygen saturation is displayed numerically at well displays 1506,1510 next to the $\Delta SpO_2$ label.

Advantageously the area 1528 between the first line representing measured arterial oxygen saturation 1514 and the second line representing regional oxygen saturation 1516 is shaded with varying colors to visually indicate the state of the metric, in this case, the patient's regional-to-central oxygenation saturation measurements, or $SpO_2$ delta. In an embodiment the area 1528 is shaded with, for example, a green color when no alarm or caution range is met, a yellow color when a caution range is met, and a red color when an alarm limit is met or exceeded, thereby visually alerting the user to circumstances that might require attention or clinical action. As illustrated in FIG. 15A a portion 1530 of the area 1528 between the first line representing measured arterial oxygen saturation 1514 and the second line representing regional oxygen saturation 1516 for sensor 1 is shaded to indicate that the regional oximetry measurement of the patient's left forehead entered into the caution range.

Figure 15B:
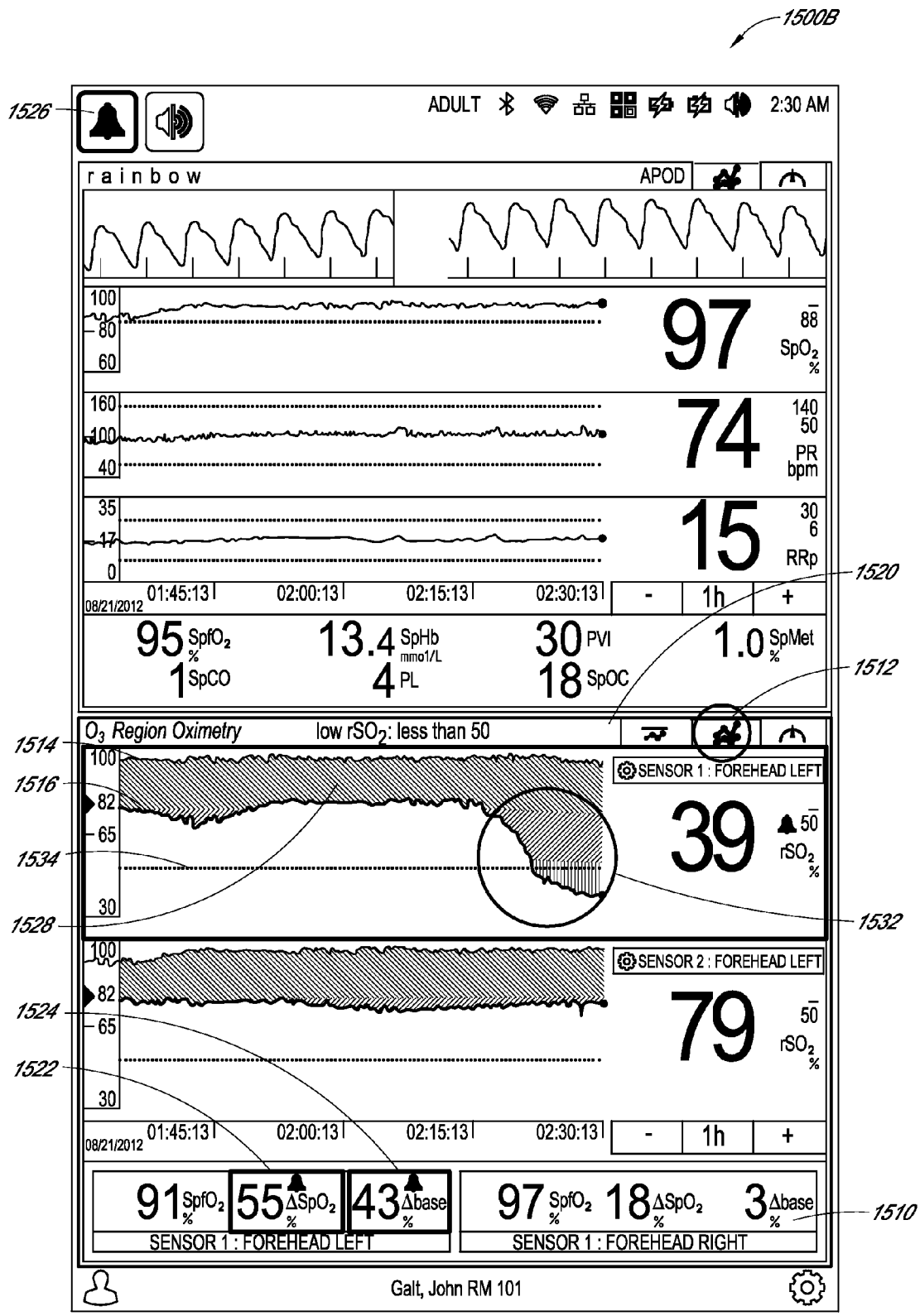

FIG. 15B illustrates an embodiment of a monitor display 1500B configured as the one in FIG. 15A, however multiple alarms are triggered. These include an alarm that the patient's left forehead regional oxygen saturation is less than 50 percent 1520, an alarm that the regional-to-central oxygen saturation measurements of the patient's left forehead region differ by 55 percentage points 1522, and an alarm that the patient's left forehead regional oxygen saturation is 43 percentage points below the patient's baseline 1524. In an embodiment the alarm conditions are highlighted visually with bold borders that are, for example, bright red in color. Additionally the alarm silence icon 1526 is illuminated in, for example, bright red. The alarm silence icon 1526 is an indicator as well as a functional button. It always indicates the presence (or lack of presence) of alarms, and it can be used to temporarily suspend audible alarms for a predetermined amount of time, known as the silence duration. When the alarm silence icon is illuminated red, it signals that there is currently at least one active alarm that has not been silenced.

As previously described the area 1528 between the first line representing measured arterial oxygen saturation 1514 and the second line representing regional oxygen saturation 1516 is shaded with varying colors to visually indicate the state of the metric, in this case, the patient's regional-to-central oxygenation saturation measurements, or $SpO_2$ delta. As illustrated in FIG. 15B a portion 1532 of the area 1528 between the first line representing measured arterial oxygen saturation 1514 and the second line representing regional oxygen saturation 1516 for sensor 1 is shaded to indicate that the regional oximetry measurement of the patient's left forehead entered into the caution range and into the alarm limit range. For easy reference, a dotted line 1534 indicates the alarm limit as set by the user.

A regional oximetry user interface has been disclosed in detail in connection with various embodiments. These embodiments are disclosed by way of examples only and not to limit the scope of the claims that follow. One of ordinary skill in the art will appreciate from the disclosure herein any variations and modifications.

The term "and/or" herein has its broadest least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Although the foregoing has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the description of the preferred embodiments, but is to be defined by reference to the claims.

Additionally, all publications, patents, and patent applications mentioned in this specification are herein incorporated by reference to the same extent as if each individual publication, patent, or patent application was specifically and individually indicated to be incorporated by reference.

What is claimed is:

1. A regional oximetry system comprising:
   a display; and
   at least one processor, the processor causing a plurality of views to be displayed on the display, each view configured to occupy at least a portion of the display, each of the views adapted to present data responsive to at least one physiological signal;
   a first sensor port configured to receive at least a first physiological signal representative of a regional tissue oxygenation level;
   a second sensor port configured to receive at least a second physiological signal representative of an arterial oxygen saturation level;
   wherein a first view presents a first trend graph of the first physiological signal and a second trend graph of the second physiological signal, and wherein the first trend graph and the second trend graph are aligned such that an area between the first trend graph and the second trend graph is representative of a differential analysis of regional-to-central oxygen saturation,
   wherein the processor determines a numerical representation of a currently-measured differential analysis of regional-to-central oxygen saturation, and wherein a second view presents the numerical representation of the currently-measured differential analysis of regional-to-central oxygen saturation.

2. The regional oximetry system according to claim 1 wherein the first trend graph is presented in a first color and the second trend graph is presented in a second color.

3. The regional oximetry system according to claim 1 wherein the display presents both the first view and the second view at the same time.

4. The regional oximetry system according to claim 1 wherein the processor determines whether a regional-to-central saturation measurement is within an acceptable range, a caution range, or an alarm range, and wherein the area between the first trend graph and the second trend graph is shaded a first color when the regional-to-central oxygen saturation measurement is within the acceptable range, a second color when the regional-to-central oxygen saturation measurement is within the caution range, and a third color when the regional-to-central oxygen saturation measurement is in the alarm range.

5. The regional oximetry system according to claim 4 wherein the first color is a shade of green, the second color is a shade of yellow, and the third color is a shade of red.

6. The regional oximetry system according to claim 4 wherein the acceptable range, caution range, and alarm range are configurable.

7. The regional oximetry system according to claim 1 wherein the first view presents an alarm limit line.

8. The regional oximetry system according to claim 1 further comprising a sensor module, and wherein the first physiological signal and the second physiological signal are provided from the sensor module.

9. The regional oximetry system according to claim 1 further comprising a first sensor module and a second sensor module, and wherein the first physiological signal is provided from the first sensor module and the second physiological signal is provided from the second sensor module.

10. A regional oximetry user interface method comprising:
  obtaining a first waveform responsive to a physiological signal representative of a regional tissue oxygenation level;
  obtaining a second waveform responsive to a physiological signal representative of an arterial oxygen saturation level;
  determining, using at least one processor, a data trend responsive to the first physiological signal;
  determining, using the at least one processor, a data trend responsive to the second physiological signal;
  determining, using the at least one processor, a difference between the data trend responsive to the first physiological signal and the data trend responsive to the second physiological signal;
  presenting, in a first display view, the determined data trends responsive to the first and second physiological signals; and
  presenting, in a second display view, the determined difference between the data trend responsive to the first and second physiological signals.

11. The regional oximetry user interface method according to claim 10 further comprising determining whether the difference between the data trend responsive to the first and second physiological signals is in an acceptable range, in a caution range, or in an alarm range.

12. The regional oximetry user interface method according to claim 11 further comprising shading with at least one color, in the first display view, an area between the data trends responsive to the first and second physiological signals, wherein the at least one color of the shading is determined by the determined range in which the difference between the data trend responsive to the first and second physiological signals is located.

* * * * *